US011819443B2

(12) United States Patent
Hansen et al.

(10) Patent No.: US 11,819,443 B2
(45) Date of Patent: *Nov. 21, 2023

(54) MOISTURE DETECTING BASE PLATE FOR A MEDICAL APPLIANCE AND A SYSTEM FOR DETERMINING MOISTURE PROPAGATION IN A BASE PLATE AND/OR A SENSOR ASSEMBLY PART

(71) Applicant: Coloplast A/S, Humlebaek (DK)

(72) Inventors: Jais Ask Hansen, Jaegerspris (DK); Finn Speiermann, Virum (DK); Niels Hvid, Vedbaek (DK); Lars Erup Larsen, Maaloev (DK)

(73) Assignee: Coloplast A/S, Humlebaek (DK)

( * ) Notice: Subject to any disclaimer, the term of this patent is extended or adjusted under 35 U.S.C. 154(b) by 581 days.

This patent is subject to a terminal disclaimer.

(21) Appl. No.: 16/955,788

(22) PCT Filed: Dec. 20, 2018

(86) PCT No.: PCT/DK2018/050380
§ 371 (c)(1),
(2) Date: Jun. 19, 2020

(87) PCT Pub. No.: WO2019/120424
PCT Pub. Date: Jun. 27, 2019

(65) Prior Publication Data
US 2021/0361465 A1   Nov. 25, 2021

(30) Foreign Application Priority Data

Dec. 22, 2017  (DK) .......................... PA 2017 70978

(51) Int. Cl.
*A61F 5/443*   (2006.01)
*A61B 5/00*   (2006.01)
*A61F 5/44*   (2006.01)

(52) U.S. Cl.
CPC ............ *A61F 5/443* (2013.01); *A61B 5/0002* (2013.01); *A61B 5/4851* (2013.01);
(Continued)

(58) Field of Classification Search
CPC ...... A61F 5/443; A61F 5/4404; A61B 5/0002; A61B 5/4851; A61B 2560/0214; A61B 2560/04
(Continued)

(56) References Cited

U.S. PATENT DOCUMENTS

| 2,054,535 | A | 9/1936 | Diack |
| 2,327,514 | A | 8/1943 | Fenwick |

(Continued)

FOREIGN PATENT DOCUMENTS

| CN | 103269668 A | 8/2013 |
| CN | 203786580 U | 8/2014 |

(Continued)

OTHER PUBLICATIONS

Waleed Shinwari et al., "Microfabricated Reference Electrodes and their Biosensing Applications", Sensors, vol. 10, 2010, pp. 1679-1715.

(Continued)

*Primary Examiner* — Christopher A Flory
(74) *Attorney, Agent, or Firm* — Coloplast Corp., Coloplast A/S; Nick Baumann

(57) ABSTRACT

The disclosure relates to a system for determining and signalling moisture propagation in an adhesive material layer of a base plate and/or a sensor assembly part for an ostomy appliance. The disclosure further relates to aspects of a base plate and/or a sensor assembly part for an ostomy appliance and its use in such a system.

48 Claims, 8 Drawing Sheets

(52) U.S. Cl.
CPC .... *A61F 5/4404* (2013.01); *A61B 2560/0214* (2013.01); *A61B 2560/04* (2013.01)

(58) Field of Classification Search
USPC ........................................................ 604/344
See application file for complete search history.

(56) References Cited

U.S. PATENT DOCUMENTS

| | | |
|---|---|---|
| 2,542,233 A | 2/1951 | Carroll |
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,197,895 A | 3/1993 | Stupecky |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries, Jr. et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,103,033 A | 8/2000 | Say et al. |
| 6,135,986 A | 10/2000 | Leisner et al. |
| 6,165,005 A | 12/2000 | Mills et al. |
| 6,171,289 B1 | 1/2001 | Millot et al. |
| 6,206,864 B1 | 3/2001 | Kavanagh et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von Dyck et al. |
| 6,520,943 B1 | 2/2003 | Wagner |
| 6,659,989 B1 | 12/2003 | Otto |
| 6,764,474 B2 | 7/2004 | Nielsen et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | von Bulow et al. |
| 7,347,844 B2 | 3/2008 | Cline et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Oelund et al. |
| 8,409,158 B2 | 4/2013 | Edvardsen et al. |
| 8,449,471 B2 | 5/2013 | Tran |
| 8,500,718 B2 | 8/2013 | Locke et al. |
| 8,632,492 B2 | 1/2014 | DeLegge |
| 8,680,991 B2 | 3/2014 | Tran |
| 8,684,982 B2 | 4/2014 | Nguyen-DeMary et al. |
| 8,740,865 B2 | 6/2014 | Krystek et al. |
| 8,795,257 B2 | 8/2014 | Coulthard et al. |
| 8,821,464 B2 | 9/2014 | Hanuka et al. |
| 8,975,465 B2 | 3/2015 | Hong et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,406,525 B2 | 8/2022 | Seres et al. |
| 11,471,318 B2 | 10/2022 | Hansen et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 | 4/2004 | Kaylor et al. |
| 2004/0100376 A1 | 5/2004 | Lye et al. |
| 2004/0106908 A1 | 6/2004 | Leise, Jr. et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | von Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries, Jr. et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |

(56) References Cited

U.S. PATENT DOCUMENTS

| | | |
|---|---|---|
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0036206 A1 | 2/2010 | Lorio |
| 2010/0072271 A1 | 3/2010 | Thorstensson |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1 | 11/2012 | Nguyen-DeMary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0261575 A1 | 10/2013 | Kiyoshi |
| 2013/0303867 A1 | 11/2013 | Elfstrom et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0284084 A1 | 9/2016 | Gurcan et al. |
| 2016/0305776 A1 | 10/2016 | Mårtensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079576 A1 | 3/2017 | Stroebech et al. |
| 2017/0140103 A1 | 5/2017 | Angelides |
| 2017/0156920 A1 | 6/2017 | Hunt et al. |
| 2017/0262986 A1 | 9/2017 | Xiong et al. |
| 2017/0340474 A1 | 11/2017 | Thirstrup et al. |
| 2017/0348137 A1 | 12/2017 | Hvid et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0078163 A1 | 3/2018 | Welch |
| 2018/0171183 A1 | 6/2018 | Sakurai et al. |
| 2019/0099552 A1 | 4/2019 | Zhang et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Muñoz Herencia |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |

(56) References Cited

U.S. PATENT DOCUMENTS

| | | |
|---|---|---|
| 2021/0386368 A1 | 12/2021 | Carlsson et al. |
| 2022/0000652 A1 | 1/2022 | Thirstrup et al. |
| 2022/031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0416397 A1 | 3/1991 |
| EP | 0373782 B1 | 10/1994 |
| EP | 0800804 B1 | 6/2003 |
| EP | 0850076 B1 | 4/2005 |
| EP | 1188157 B1 | 12/2005 |
| EP | 2108345 A1 | 10/2009 |
| EP | 1275357 B1 | 3/2011 |
| EP | 2489561 A2 | 8/2012 |
| EP | 2601915 A1 | 6/2013 |
| EP | 2654646 B1 | 7/2016 |
| EP | 3213727 B1 | 12/2019 |
| EP | 3064179 B1 | 9/2021 |
| GB | 2219679 A | 12/1989 |
| GB | 2343628 A1 | 5/2000 |
| GB | 2465742 A1 | 6/2010 |
| GB | 2542093 A | 3/2017 |
| JP | H0474882 A | 3/1992 |
| JP | H06152077 A | 5/1994 |
| JP | H0910184 A | 1/1997 |
| JP | 11128352 A | 5/1999 |
| JP | 2000093448 A | 4/2000 |
| JP | 2001087299 A | 4/2001 |
| JP | 2002055074 A2 | 2/2002 |
| JP | 2002224093 A2 | 8/2002 |
| JP | 2005323981 A2 | 11/2005 |
| JP | 2007319561 A | 12/2007 |
| JP | 2014033745 A | 2/2014 |
| JP | 2014054368 A | 3/2014 |
| JP | 2014507182 A | 3/2014 |
| KR | 20120003987 A | 1/2012 |
| RU | 2527155 C2 | 8/2014 |
| TW | 201201783 A | 1/2012 |
| WO | 9415562 A1 | 7/1994 |
| WO | 9710012 A1 | 3/1997 |
| WO | 1999033037 A1 | 7/1999 |
| WO | 1999036017 A1 | 7/1999 |
| WO | 0079497 A1 | 12/2000 |
| WO | 2001013830 A1 | 3/2001 |
| WO | 2001050996 A1 | 7/2001 |
| WO | 02052302 A2 | 7/2002 |
| WO | 02099765 A1 | 12/2002 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007098762 A1 | 9/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 11105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2013013197 A1 | 1/2013 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2016166731 A1 | 10/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017088153 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019161863 A1 | 8/2019 |

OTHER PUBLICATIONS

"Burns, S. et al., Inkjet Printing of Thin-Film Transistor Circuits. MRS Bulletin (2003) 28: 11, 829-834".
Self-Sealing Therapy (Self-Sealing Therapy Ostomy Pouch, https://www.sbir.gov/sbirsearch/detail/5517, accessed Feb. 21, 2018, captured Oct. 20, 2011).
"Ultra-Low-Power, Single-Supply Op Amp + Comparator + Reference", Maxim Integrated Products, 2001, pp. 1-12.
Ignjatovic et al. "An Interface Circuit for Measuring Capacitance Changes Based Upon Capacitance-to-Duty Cycle (CDC) Converter" IEEE Sensors Journal, 2005, vol. 5 No. 3, pp. 403-405.
Akar et al. "A wireless batch sealed absolute capacitive pressure sensor" Sensors and Actuators A, 2001, vol. 95, pp. 29-38.
Zeng et al. "Time domain characterization of oscillating sensors: Application of frequency counting to resonance frequency determination" Review of scientific instruments, 2002, vol. 73 No. 12, pp. 4375-4380.
Ong et al. "Design and application of a wireless, passive, resonant-circuit environmental monitoring sensor" Sensors and Actuators A, 2001, vol. 93, pp. 33-43.
Ashrafi et al. "A high precision method for measuring very small capacitance changes" Review of scientific Instruments, 1999, vol. 70 No. 8, pp. 3483-3487.
Notice of Third Party Submission Under 37 CFR 1.290 in U.S. Appl. No. 16/686,233, dated Oct. 7, 2020, 24 pages.
Communication pursuant to Rule 114(2) EPC reporting Observations by a Third Party filed in EP Application No. 18830373.9-1122, dated Sep. 16, 2020, 21 pages.

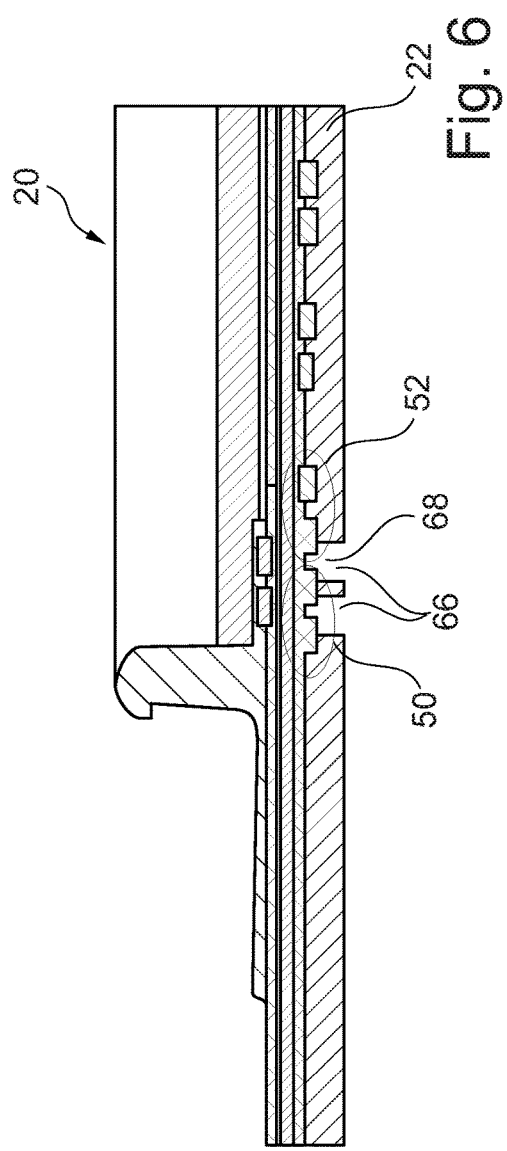
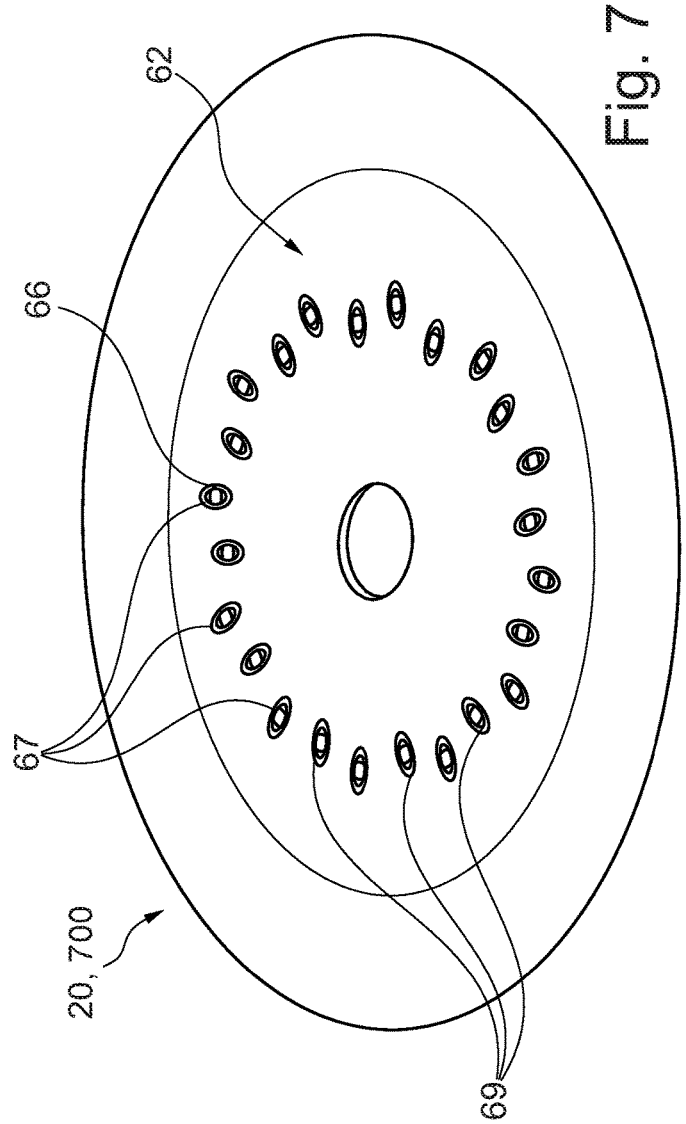

MOISTURE DETECTING BASE PLATE FOR A MEDICAL APPLIANCE AND A SYSTEM FOR DETERMINING MOISTURE PROPAGATION IN A BASE PLATE AND/OR A SENSOR ASSEMBLY PART

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output 'underneath' the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY

The present disclosure provides aspects of a base plate and/or a sensor assembly part for an ostomy appliance according to claim 1. Further disclosed is a system for determining and signalling moisture propagation in an adhesive material layer of a base plate and/or a sensor assembly part for an ostomy appliance according to claim 32.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 6 is a cross-sectional view of a portion of the base plate according to one embodiment.

FIG. 7 is a schematic perspective view of one embodiment of the base plate.

DETAILED DESCRIPTION

Figure 1:
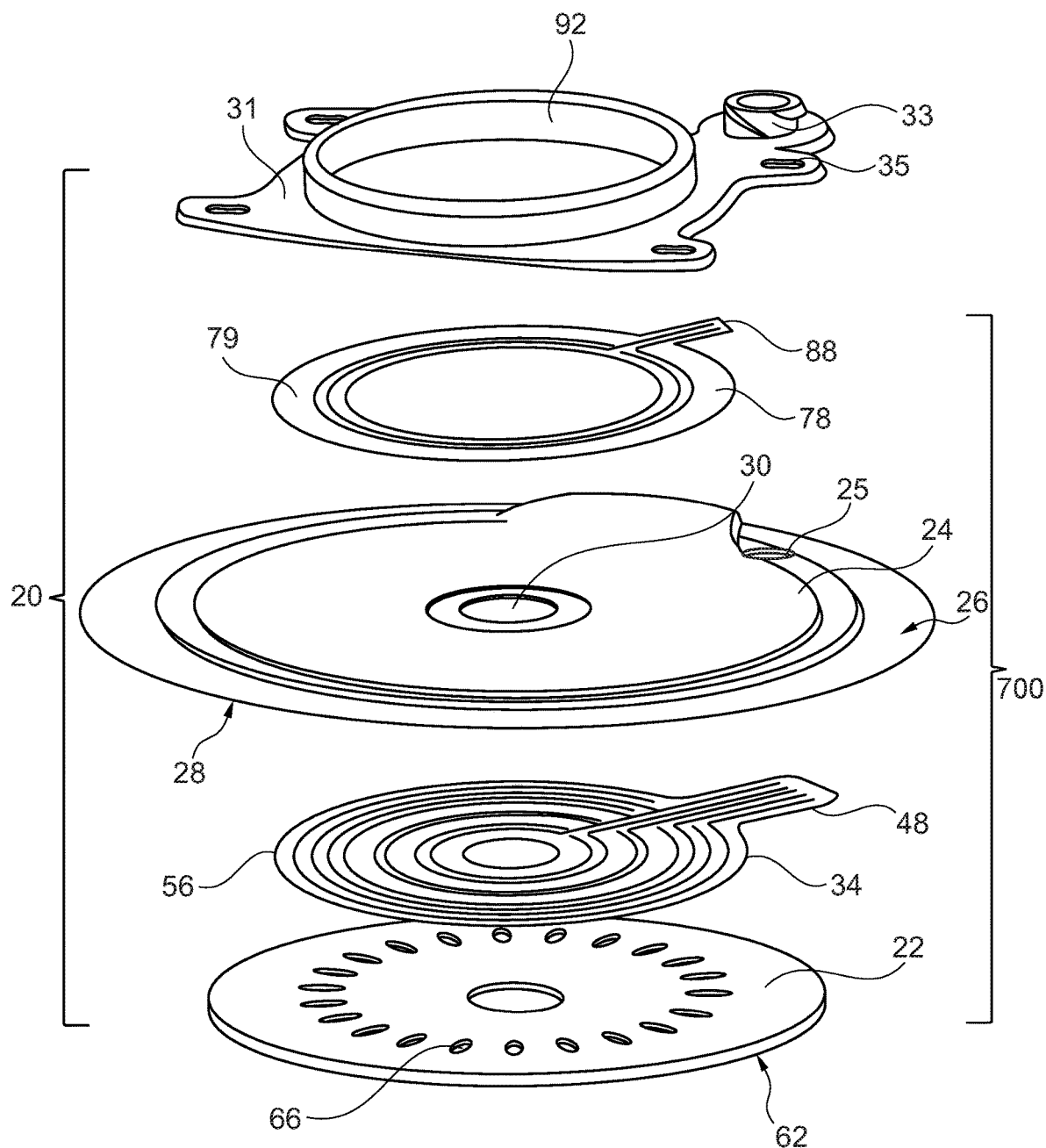
FIG. 1 is an exploded, perspective view of one embodiment of a base plate according to the first aspect of the disclosure.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"-moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Embodiments of the disclosure provides a base plate for an ostomy appliance which facilitates reliable determination of the nature, severity and rapidness of moisture propagation in the adhesive material provided for attaching the base plate to the skin surface of a user. Depending on the nature of the pattern of moisture propagation in the adhesive, the base plate of the disclosure helps provide information to the user about the type of failure, and in turn helps provide an indication to the user of the severity and thus the remaining time frame for replacing the appliance for a fresh one without experiencing severe leakage. A first moisture propagation pattern can correspond to a rapidly evolving adhesive failure, which requires immediate attention to avoid a severe leakage incident, e.g. one requiring change of clothes because of soiling from stomal output. Another, different moisture propagation pattern can correspond to a relatively slow evolving, general weakening of the adhesion capacity of the adhesive material, which informs the user that—while perhaps not imminent—replacement of the appliance for a fresh one is required because the appliance is approaching an "end-of-life" condition. Yet other and/or "intermediate" moisture propagation patterns can be envisioned and determined to indicate other conditions of the layer of adhesive material etc.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

Thus, in one aspect, the present disclosure relates to a base plate and/or a sensor assembly part for an ostomy appliance, comprising at least a first layer of an adhesive material adapted for attachment of the base plate and/or the sensor assembly part to the skin surface of a user; a backing layer comprising a film material forming a distal and a proximal surface of the backing layer, wherein a stoma-receiving opening extending through the base plate and/or the sensor assembly part is provided in a center portion of the base plate and/or the sensor assembly part surrounding the stoma-receiving opening. The base plate and/or the sensor assembly part further includes a first sensor element comprising at least one sensor pair. The sensor pair comprises a first sensor and a second sensor. Each of the at least first sensor and the second sensor is connected to a control unit interface, such that an electrical signal can be conducted between a respective sensor and the control unit interface. The first sensor element is provided between the first layer of adhesive material and the proximal surface of the backing layer. Moreover, each of the first sensor and the second sensor of the sensor pair comprises a conductor electrode and a ground electrode. Also, the second sensor of the sensor pair is located at a greater radial distance from the stoma-receiving opening than the first sensor of the sensor pair.

In embodiments, the center portion of the base plate and/or the sensor assembly part is immediately adjacent to and surrounding the stoma-receiving opening of the base plate and/or the sensor assembly part. In embodiments, the layer of adhesive material can comprise more than one kind of adhesive material (i.e. "a composition" of adhesive materials).

In embodiments, the conductor electrode and the ground electrode of each of the first sensor and the second sensor form a pair of at least partially co-extending electrodes. Thereby, the pair of electrodes are provided next to each other and follow each other over at least some of their extent in the first sensor element.

In embodiments, the at least first sensor is adapted as a detection sensor and configured to detect moisture propagation in the center portion of the base plate and/or the sensor assembly part. The second sensor is adapted as a reference sensor configured to detect moisture propagation in an outlying portion of the base plate and/or the sensor assembly part. The outlying portion is a different portion of the base plate and/or the sensor assembly part than the center portion. The outlying portion and the center portion combine to form the entire extent of the base plate and/or the sensor assembly part. The outlying portion surrounds the center portion of the base plate and/or the sensor assembly part. In embodiments, the outlying portion is provided annularly around the center portion of the base plate and/or the sensor assembly part.

In embodiments, each of the first and the second sensor includes a detecting portion provided around the stoma-receiving opening and an extension portion extending from the detecting portion of each sensor to the control unit interface.

In embodiments, in the extension portion, each electrode comprises an insulating element covering at least a portion of its exposed surface. More portions of an electrode can be covered by insulating elements depending on the specific configuration of the electrodes in the first sensor element.

In embodiments, the first sensor is a radially innermost detection sensor, and the reference sensor is a radially outermost reference sensor.

The control unit interface is configured for connection to a control unit. The control unit is a separate unit configured to combine/couple with the base plate and/or the sensor assembly part of the first aspect of the disclosure. The control unit is adapted to measure or detect and determine the meaning of changes in the input received from a first sensor and from a second sensor. If/when a significant change occurs, this can for example signal a rapid or sudden increase in the quantity of moisture (incl. in liquid form) present at a detection sensor. In case the reference sensor does not simultaneously detect a similar signal as was detected by the detection sensor, it signifies that the increase in moisture level is not also present at the location of the reference sensor. The determination by the control unit of this moisture propagation pattern is considered unusual and likely represents a beginning leakage. However, the determined pattern also indicates that the increase in moisture level (e.g. leakage) has not progressed as far from the stoma-receiving opening as to reach the location of the reference sensor. The user is thereby provided with an "early" warning, allowing him/her enough time to replace the ostomy appliance (or take other measures) and avoid a severe leakage incident. The control unit is further described below in relation to the second aspect of the disclosure.

According to the present disclosure, the "warning time", i.e. the amount of time available for the user to react to a determined moisture propagation pattern can be adapted by controlling different factors and/or parameters. These can include, but are not limited to, controlling; how far from the stoma-receiving opening of the base plate and/or the sensor assembly part a detection sensor is located; applying more than one detection sensor at different distances from the stoma-receiving opening; determining changes in measurements between two or more detection sensors, and by providing a variety of different algorithms for use by the control unit, which can provide determination options applicable to more specific moisture propagation patterns.

Experience shows that beginning leakage or the presence of any unusual propagation of moisture generally occurs starting from the stoma. Thus, an initial attack of propagating moisture practically always takes place at an innermost edge or rim portion of the base plate at the stoma-receiving opening. However, the moisture can continue its propagation from the edge or rim portion in any or all radial directions of the base plate. The moisture propagation can be much more pronounced in some radial direction(s) than in other radial directions.

In the context of the present disclosure, it is envisioned that changes in a parameter, e.g. changes in the resistance measured at a detection sensor and/or in the resistance measured at the reference sensor, occur when an amount of moisture emerges on the skin surface of the user around the stoma and propagates into the adhesive material of the base plate and/or the sensor assembly part. A quantity of emerged moisture on the skin surface in effect provides an electric conductor, such that the moisture creates a conductive path between the conductor electrode and the ground electrode. When this happens, the resistance output of the sensor changes, in some situations significantly. If an amount of moisture has emerged and propagated into the adhesive material of the base plate and/or the sensor assembly part and into contact with a detection sensor but not with the reference sensor, the resistance measured at each of the sensors will be significantly dissimilar.

In embodiments, the at least first detection sensor is provided in an at least partly annular configuration around the stoma-receiving opening. Thus, the detection sensor can be provided such that the detecting portion surrounds the stoma-receiving opening, generally in a circle form or circular manner, however without the electrode pair completely forming a full 360° circle. Instead, in embodiments, the partly annular configuration should be interpreted such that an annularly configured detection sensor includes a relatively small portion where it is "open". In embodiments, the extension portion extends from the detecting portion of the sensor at or adjacent the "open" portion of the detection sensor. These embodiments provide for a reliable and intuitive construction of the first sensor element and facilitates its manufacture as described otherwise in this disclosure.

In embodiments, the pair of at least partially co-extending electrodes of each sensor is configured at least partly annularly around the stoma-receiving opening of the base plate and/or the sensor assembly part. Thereby, the conductor electrode and the ground electrode of a sensor both extend generally around the stoma-receiving opening of the base plate and/or the sensor assembly part, but may also form an "open" portion as described for the first detection sensor.

In embodiments, the conductor electrode and the ground electrode each are provided as line electrodes. The term "line electrode" should be interpreted as an electrode of a continuous extent. In one embodiment, the extent in one direction of the electrode is at least five times the extent of the electrode in a direction substantially perpendicular to the first direction, e.g. in one interpretation the electrode is five times or more longer than it is wide. In embodiments, the conductor electrode and the ground electrode are provided next to each other in a continuous manner at least in the detecting portion of each sensor. In one embodiment, the conductor electrode and the ground electrode are provided such as to maintain a constant distance between them, at least in the detecting portion of each sensor. In embodiments, the conductor electrode and the ground electrode are provided parallel to each other, at least in the detecting portion of each sensor. In some interpretations, the electrodes can be considered similar to conductive wires or to traces/tracks of an electronic circuit, e.g. such as those on a printed circuit board. Such embodiments provide for the electrodes to provide for easy and continuous comparability of the measured parameter. Moreover, variation of the distance between the conductor electrode and the ground electrode also provides an option for controlling the sensitivity of detecting potential leakage of the base plate and/or the sensor assembly part.

In embodiments, the at least first detection sensor is located at the center portion of the base plate and/or the sensor assembly part. In embodiments, the at least first detection sensor is adapted to coincide with the center portion of the base plate and/or the sensor assembly part, whereby the first detection sensor extends over a major portion of the area or zone of the base plate and/or the sensor assembly part defining the center portion. In embodiments, the center portion of the base plate and/or the sensor assembly part is defined as a portion of the base plate and/or the sensor assembly part from a rim of the stoma-receiving opening and up to (and incl.) a radial distance of up to 50 mm therefrom, such as 45 mm therefrom, such as 40 mm therefrom, such as 35 mm therefrom, such as 30 mm therefrom, such as 25 mm therefrom, such as 20 mm therefrom. In embodiments, a diameter of the stoma-receiving opening is adaptable to between 20-70 mm. In embodiments, the center portion is alternatively or additionally defined as a portion of the base plate and/or the sensor assembly part comprising a second skin-friendly adhesive around the stoma-receiving opening. In embodiments, the center portion is alternatively or additionally defined as a portion of the base plate and/or the sensor assembly part radially inside of a first half of an annular coupling means attached to the distal surface of the backing layer. Among other things, placing the at least first detection sensor in the center portion of the base plate and/or the sensor assembly part is advantageous in that it provides for very early detection of potential leakage, which is helpful as some users may experience rapid failure of the adhesive resulting in a leakage incident, when the stomal output has propagated underneath the layer of adhesive material. Moreover, placing the at least first detection sensor in the center portion of the base plate and/or the sensor assembly part provides a relatively simple construction for manufacture, while additionally being intuitive to users.

In embodiments, the reference sensor is provided at an outer rim portion of the first sensor element. In embodiments, the outer rim portion of the first sensor element is defined at a radially outermost edge portion of the base plate and/or the sensor assembly part. Placing or providing the reference sensor at the outer rim portion of the first sensor element is advantageous in that it helps provide a relatively simple construction for manufacture, while additionally being intuitive to users.

In embodiments, the reference sensor is provided in an essentially concentric manner around the first detection sensor. This provides for possible early detection of leakage caused by propagating moisture, such as aggressive visceral fluids exiting from the stoma in any radial direction in the layer of adhesive of the base plate and/or the sensor assembly part.

In embodiments, the first sensor element further includes one or more additional detection sensors, each of the additional detection sensors being provided at different radial distances from the stoma-receiving opening. The one or more additional detection sensors according to these embodiments help provide for a further increased sensitivity of the base plate and/or the sensor assembly part in determining if and how moisture is propagating in or under the layer of adhesive of the base plate and/or the sensor assembly part, such as to provide an even more precise indication of potential or upcoming leakage, or, alternatively, that the ostomy appliance is approaching an end-of-life condition.

In embodiments, the first sensor element comprises two or more detection sensors. Each of the further detection sensor(s) is provided concentrically around the first detection sensor. Moreover, the first sensor element is configured such that two detection sensors share one concentrically provided ground electrode. Each additional detection sensor is adaptable to provide an individual indication (input from an individual location in the layer of adhesive) to the control unit. For example: if a first, radially innermost detection sensor indicates a sudden abrupt propagation of moisture at its location and is followed by a similar indication from a second detection sensor, located radially farther away from the stoma-receiving opening, the ensuing assumption is that this moisture propagation pattern is not related to or caused by a simple, continuous uptake of moisture (incl. sweat) from the skin, but indeed very likely to an unusual propagation of stomal output underneath the adhesive of the base plate and/or the sensor assembly part.

In embodiments, one function of the ground electrode is basically to provide a return path for an electric current applied via the conductor electrode, such that a closed loop electric circuit is established. Thus, in embodiments, one (one and only one) ground electrode is adapted to form the ground electrode of the pair of electrodes of a first detection sensor, and to further form the ground electrode of the pair of electrodes of a second (different/additional) detection sensor. This is particularly, but not exclusively, advantageous in embodiments wherein the at least two detection sensors are provided concentrically in relation to each other. In other words, the same (single) ground electrode can be configured as the ground electrode of the electrode pair of two neighboring and/or adjacent detection sensors. As the ground electrode functions to establish a closed loop circuit, one single ground electrode can be used by more than one detection sensor (i.e. be "paired" with more than one conductor electrode).

By sharing a ground electrode, i.e. adapting it to function with the conductor electrode of two different, neighboring detection sensors, space is saved allowing the first sensor element to include a relatively higher number of detection sensors. Moreover, the construction of the first sensor element for manufacture is thereby less complex, easing size and tolerance requirements, and it is less costly to produce.

In embodiments, knowing the distance between each of a plurality of individual detection sensors can additionally help provide an indication of the pace of the moisture propagation, which in turn can help determine the nature and severity of the moisture propagation. Thus, in embodiments the distance between a first and a second detection sensor is predetermined at manufacture. In embodiments, the distance between a first and a second sensor is substantially identical to the distance between the second sensor and a third sensor and so forth. In other embodiments, the distance between the first sensor and the second sensor (and/or any further detection sensors) varies. In one embodiment, the distance between any two detection sensors increases linearly such that the distance is greatest between sensors which are closer to an outer rim portion of the first sensor element than to the stoma-receiving opening of the base plate. In addition, the pace of moisture propagation can further be correlated with empirical data to help make the determination.

In embodiments, the extension portion comprises a linear, common ground electrode which is connected to a ground electrode of each detection sensor, and optionally further connected to the ground electrode of the reference sensor. The extension portion extends from the detecting portion of each sensor to the control unit interface. The extension portion provides a conductive path from the electrode pairs of each sensor to the control unit interface, such that an electrical signal can be conducted from a respective sensor to the control unit interface. In embodiments, the conductor electrode of the one or more detection sensors extends continuously from the detecting portion to the control unit interface. By "continuously", it is to be understood that the electrode does not include any interrupted portions or sections. Additionally or alternatively, "continuously" can be interpreted such that even an electrode of a considerable, relative dimension in one direction is formed to be integral throughout its extent, such that electric current can be conducted reliably and sustainably throughout the electrode's dimensional extent.

In embodiments, wherein the base plate and/or the sensor assembly part comprises more than one detection sensor, the conductor electrode of each detection sensor extends individually and continuously to the control unit interface. Similarly, in embodiments, the conductor electrode of the reference sensor extends individually and continuously from the detecting portion to the control unit interface. Conversely, in embodiments, the ground electrode of the one or more detection sensors and/or the reference sensor is configured as a linear, common (one single) ground electrode extending in the extension portion. In other words, in such embodiments the portion of the ground electrode of each of the sensors in the extension portion forms a single conductive line or track. The linear, common ground electrode formed by the single conductive line or track is further connected to the ground electrode of each sensor by a connection portion of electrode track. In embodiments, the linear, common ground electrode comprises a plurality (two or more) of connection portions corresponding to the number of detection sensors plus the reference sensor. In embodiments, the linear, common electrode and the plurality of connection portions combine to form a tree-like structure, with the linear, common electrode forming the "tree trunk" and the plurality of connection portions forming branches extending from the trunk. Thus, in embodiments, the linear, common ground electrode in the extension portion is connected to the ground electrode of each electrode pair and is adapted to close the circuit loop for any of the detection and/or reference sensors. Like above, at least some of the beneficial effects of these embodiments include that the sensor element is of a less complex construction, easing size and tolerance requirements and lowering manufacturing costs.

In embodiments, the first sensor element comprises a layer or a sheet component. In embodiments, the one or more detection sensor(s) and the reference sensor of the first sensor element are printed or etched onto the layer or sheet component of the first sensor element. Other ways of configuring the first sensor element with the detection sensor(s) and/or the reference sensor are acceptable, provided these do not affect their suitability as components of the base plate of an ostomy appliance. In embodiments, the layer or sheet component of the first sensor element comprises a polyurethane (PU) material and/or an ethylene vinyl acetate (EVA) material. In embodiments, the layer or sheet component of the first sensor element comprises an adhesive material for attaching the first sensor element to the proximal surface of the backing layer. In embodiments, the adhesive material is provided as a tie layer on a distal surface of the first sensor element, or on the proximal surface of the backing layer. Other ways of attaching the first sensor element to the proximal surface of the backing layer, such as including welding, are also acceptable provided the attachment or the attaching process does not influence the electrodes or any other characteristic of the first sensor element.

In embodiments, at least a portion of the layer or sheet component is adapted to be moisture permeable. In one embodiment, the entire layer or sheet component is adapted to be moisture permeable. In embodiments, only a portion of the layer or sheet component is adapted to be moisture permeable, e.g. a portion corresponding in size and shape to the center portion of the base plate or a portion corresponding to an outlying portion of the base plate and/or the sensor assembly part, and/or to an outer rim portion of the first sensor element.

In some implementations, the layer or sheet component of the first sensor element is made moisture permeable to e.g. provide for the option of embedding the electrode pairs of each of the sensors in the material of the layer or sheet component. Thus, in embodiments, the electrode pairs of the sensors are embedded in the layer or sheet component of the first sensor element. In one embodiment, the layer or sheet component comprises a planar distal surface and a planar proximal surface, and with each sensor embedded in the layer or sheet component.

In embodiments, any proximally facing portion of an electrode is configured to be approximately 1 mm from a proximal surface of the first layer of adhesive material prior to the base plate and/or the sensor assembly part being applied to the skin surface.

Embedding the electrodes in the layer or sheet component provides for the first sensor element of the base plate to be less sensitive to "allowable moisture" e.g. in the form of sweat secreting from the skin surface of the user over time. Thus, if moisture reaches the electrodes relatively quickly after the user has applied the base plate and/or the sensor assembly part to the skin surface, this is a strong indication of an unusual moisture propagation pattern such as sudden and/or rapid acting leakage underneath the adhesive. Thus, in embodiments, applying the electrodes in the sensor element approximately 1 mm from the proximal surface of the adhesive material, provides a balanced sensitivity of the first sensor element in regard to being able to distinguish between "allowable moisture" secreted relatively slowly as sweat from the skin, and rapidly emerging moisture originating from stomal output.

Other or additional parameters and factors can be controlled to adapt the base plate and/or the sensor assembly part to provide for delivering a customized or specialized indication as a reaction to the different patterns of moisture propagation. These include, but not exhaustively, providing embedded electrodes "deeper" or "shallower" in the sensor element; providing two or more electrodes at different radial distances from the stoma-receiving opening of the base plate and/or the sensor assembly part; providing two or more embedded electrodes at different "depths" in the layer or sheet component of the sensor element; controlling a thickness of the adhesive material covering the electrodes, e.g. to maintain a constant thickness of the layer of adhesive material or alternatively to vary the thickness of the layer of adhesive material across the portion covering the electrodes and/or, such as the center portion and/or the outlying portion of the base plate and/or the sensor assembly part, and by combinations of these parameters and factors.

In embodiments, each electrode of the sensors is provided in one and the same plane of the layer or sheet component. This provides a relatively simple structure of the first sensor element, which is advantageous to reduce complexity and manufacturing costs.

In embodiments, the electrodes of the sensors are printed on to one of the planar surfaces of the layer or sheet component. In one embodiment, the electrodes are printed on to the planar proximal surface of the layer or sheet component. Thereby, in some embodiments, the electrodes of the sensors can have direct contact with (are directly exposed to) the adhesive material of the base plate and/or the sensor assembly part. This provides for a direct and undelayedly sensor response when adhesive material initially covering the electrodes has deteriorated. Particularly, but not exclusively, such embodiments optimize the first sensor element for (early) sensing/detection of a sudden unusual moisture propagation pattern in the base plate and/or the sensor assembly part, and thus more directed towards "leakage" (rapid emerging moisture propagation) detection than towards "degradation" (slow emerging moisture propagation) detection.

In embodiments, the conductor electrode and/or the ground electrode comprise(s) a silver material and/or a carbon black material. In embodiments, the electrodes comprise one or more inks containing a carbon black material. In one embodiment, carbon black containing electrodes are printed onto the layer or sheet component of the first sensor element. In embodiments, a thickness of the electrodes of the first sensor element is approximately 20 μm. Alternatively, the electrodes can be applied to the first sensor element by a laminating process or by a punching process. Alternatively or additionally, the electrodes can be provided from other solution-based materials, such as organic semiconductors, inorganic semiconductors, metallic conductors, nanoparticles, nanotubes and others.

In embodiments, a second layer of adhesive material is provided on the proximal surface of the backing layer, and wherein the first sensor element is provided between the first layer of adhesive material and the second layer of adhesive material. In embodiments, the adhesive material of the second layer of adhesive material is identical to the adhesive material of the first layer of adhesive material. In embodiments, the adhesive material of the second layer of adhesive material is different than the adhesive material of the first layer of adhesive material. In embodiments, the second layer of adhesive material is adapted to be particularly resistant to stomal output. In embodiments, the second layer of adhesive material is adapted to be particularly suitable for being applied at an outlying portion of the base plate and/or the sensor assembly part, e.g. an adhesive having a high initial tack such as an acrylate-based type adhesive. In embodiments, the second adhesive is configured to cover or coincide with the center portion of the base plate and/or the sensor assembly part. In embodiments comprising both a first layer of an adhesive material and a second layer of an adhesive material, the first layer of adhesive material is advantageously adapted to be particularly resistant to stomal output, and the second layer of adhesive material is advantageously adapted to be particularly suitable for ensuring a strong adhesion to the skin surface.

Alternatively or additionally, in embodiments the first layer of adhesive material comprises a plurality of through-going openings, such that each through-going opening provides access to at least one of the electrodes of an electrode pair of a detection sensor. Thereby, each through-going opening provides a passageway for moisture to pass through the first layer of adhesive material and into contact with the at least one electrode of the detection sensor. In such implementations, the first layer of adhesive has a certain thickness. In embodiments, the thickness of the first layer of adhesive is approximately 1 mm, at least when the base plate and/or the sensor assembly part is initially applied to the skin surface. The electrodes of the detection sensor are thus not located immediately adjacent to or on the skin surface of the user. Instead, the electrodes of the detection sensor can be understood to be elevated in relation to the skin surface. This in turn provides for the electrodes of the detection sensor to be less prone and/or susceptible to slowly emerging moisture (sweat) from the skin surface. Thereby, in these embodiments, the base plate and/or the sensor assembly part is configured with particular focus on detecting "direct" leaking or outflow of stomal output from the stoma. By providing the plurality of through-going openings in the first layer of adhesive material, it is ensured that the base plate and/or the sensor assembly part has increased sensitivity to such "direct" leaking or outflow. Put simply, the plurality of through-going openings basically make it easy for the stomal output to quickly reach the electrodes of the detection sensor. In embodiments, the same or a similar effect can alternatively or additionally be achieved by applying a wicking and/or a hydrophilic material layer between the layer of the first adhesive and the first sensor element.

Particularly, but not exclusively, this is advantageous for directing the first sensor element to uses of detecting sudden leakages, or adhesive failure, in the immediate peristomal area. By applying a plurality of through-going openings, any rapid-acting or rapid-emerging amount of moisture emanating directly from the stoma can be easily and quickly detected by the first sensor element.

In embodiments, a first group of openings of the plurality of through-going openings is radially offset from a second group of openings of the plurality of through-going openings. Thereby, each through-going opening of the first group provides access to the electrode pair of a first detection sensor, and each through-going opening of the second group provides access to one of the electrodes of the first detection sensor and to one of the electrodes of a second detection sensor. This is particularly, but not exclusively, advantageous in that one of the electrodes, particularly a ground electrode, can be a common shared electrode of first and second detection sensors. This reduces the number of necessary electrodes and thus the complexity of the sensor element and manufacturing costs. Moreover, the requirements for receiving and processing data input in the control unit according to the second aspect of the disclosure can be reduced.

In embodiments, the plurality of through-going openings is distributed in a generally circular configuration around the stoma-receiving opening. In other words, each opening of the plurality of openings is located as following a pattern of a circular figure. Depending inter alia on the desired sensitivity and precision of the first sensor element, the plurality of openings can be selected accordingly. In embodiments, the plurality of openings comprises between 2-30 openings. In embodiments, the plurality of openings is even in number. In other embodiments, the plurality of openings is uneven in number. The plurality of openings is particularly advantageous when the sensors, particularly the one or more detection sensors are provided concentrically around the stoma-receiving opening and/or the center portion of the base plate and/or the sensor assembly part. In embodiments, the plurality of through-going openings is evenly distributed around the stoma-receiving opening.

In embodiments without through-going openings in the first layer of adhesive material, the base plate and/or the sensor assembly part can also be configured such that the electrodes of a detection sensor are not located immediately adjacent to, or on the skin surface of the user. Like before, the electrodes of a detection sensor can be understood to be elevated in relation to the skin surface. In embodiments, the detection sensor is covered by the adhesive material. In embodiments, the layer of adhesive material is approximately 1 mm thick, at least when the base plate and/or the sensor assembly part is initially applied to the skin surface. However, because the through-going openings are not present, the electrodes of the detection sensor are here less subjected to rapid emerging moisture outflow from the stoma. Thereby, in these embodiments, the base plate and/or the sensor assembly part is configured with particular focus on detecting "wear" of the adhesive material of the base plate and/or the sensor assembly part.

In embodiments, the base plate and/or the sensor assembly part of the first aspect of the disclosure further comprises a sacrificial material provided on the distal surface of the backing layer. In embodiments, the sacrificial material comprises a neutralizing component. In embodiments, the sacrificial material is provided as a layer located on the distal surface of the backing layer. The sacrificial material and the neutralizing component are described in more detail below.

In embodiments, the base plate and/or the sensor assembly part further comprises a second sensor element provided between the layer of sacrificial material and the distal surface of the backing layer. This is particularly advantageous in that additional security and/or certainty against leakage occurring is provided. By providing a second sensor element separate from the first sensor element and locating it between the sacrificial material and the distal surface of the backing layer, the user can be provided with an indication of the status of the sacrificial material. If/when the quantity of sacrificial material reaches a predetermined minimum value, the second sensor element signals a change in a measured or determined parameter to the control unit, which in turn can be configured to inform the user that the sacrificial material is used up, or close to being so, thereby indicating that replacement of the base plate and/or the ostomy appliance is potentially required.

In embodiments, the second sensor element comprises one or more detection sensors each comprising a pair of parallelly extending electrodes defining a detecting portion configured to be located essentially around the stoma-receiving opening. Each sensor of the second sensor element further includes an extension portion adapted to extend from the detecting portion to the control unit interface of the base plate and/or the sensor assembly part. Other attributes and/or characteristics of the first sensor element, such as the choice of material of the element itself and the material of the electrodes, can be applied analogously to the second sensor element. In embodiments, the second sensor element is provided as a generally annular or ring-shaped component, e.g. provided as a cut-out of a film or foil of EVA or PU. In embodiments, the second sensor element includes a single (one and only one) sensor. Thus, in embodiments, the addition of the second sensor element can be understood to provide the base plate and/or the sensor assembly part also with an additional "wear indicator", in the sense that the layer of sacrificial material is equipped with its "own" dedicated sensor element for detecting when the sacrificial material has eroded away fully, or to a certain pre-determined extent. The latter can be influenced by a variety of controllable parameters/factors, such as the nature of the sacrificial material, the "depth" and orientation of the electrodes of the second sensor element and/or the radial distance by which the sensor(s) of the second sensor element is separated from the stoma-receiving opening of the base plate and/or the sensor assembly part. Particularly, with regard to the latter factor, the greater the radial distance, the longer it assumedly takes before stomal output has eroded away the sacrificial material.

In embodiments, the electrodes of the one or more detection sensors of the second sensor element are adapted to face or point towards the distal surface of the backing layer. This construction provides for an "output trap" if/when the sacrificial material has eroded away.

In embodiments, one or more of the backing layer, the first sensor element and the second sensor element describes a generally circular figure, however further comprising a flap portion extending radially away from an outermost rim portion of the circular figure, the flap portion in at least some embodiments configured to coincide with the extension portion of the sensors. The flap portion can be interpreted as a cantilevered portion of the first and/or second sensor element, extending off an outermost edge or rim of the sensor element. Particularly, but not exclusively, the flap portion is adapted to provide or function as a base for the control unit interface distanced from any rapid-emerging moisture or leakage from the stoma, and easily accessible. Moreover, the flap portion provides a suitable location for connection of a control unit to the base plate and/or the sensor assembly part in a system according to the second aspect of the disclosure.

In embodiments, the backing layer comprises a woven or a non-woven material. In one embodiment, the backing layer is a thermoplastic polymer film. In one embodiments, the backing layer comprises an elastic material. In one embodiment, the backing layer is suitably capable of transmitting moisture and may e.g. be made from polymers such as polyolefin types e.g. PE, PP or polybutylene, polyamide such as nylon, polyurethane, polyvinyl acetate, polyvinyl chloride, fluorinated polyvinyl compound, polyvinylidene chloride, polyvinyl alcohol, ethylene vinyl acetate, cellulose acetate or other thermoplastic polysaccharides, polyether block amides such as PEBAX® from Arkema, France, block copolymers like styrene-isoprene-styrene block copolymers or ethylene acrylate block copolymers, polyesters such as polyethylene terephthalate (PET) or derivates thereof and any laminates from such polymers. In other embodiments, the backing layer comprises a thin foam layer made from e.g. polyurethane, polyethylene or polyvinyl acetate.

In embodiments, the base plate further comprises a first half of a coupling means configured for releasable coupling with a second half of a coupling means on a stomal waste collecting bag, the first half of the coupling means being attached to the distal surface of the backing layer.

In embodiments, the first coupling half is a flange adapted to provide a surface for attaching the second coupling half in the form of an adhesive flange provided on a stomal output collecting bag. In embodiments, the first half of the coupling is configured as a flexible, planar annular flange optionally comprising an adhesive. The first coupling half is adapted to couple with the second coupling half provided around an inlet opening of a stomal output collecting bag by means of an adhesive. The adhesive coupling may provide a releasable or a permanent adhesive coupling engagement between the base plate and the collecting bag.

In embodiments, the first coupling half is an annular ring comprising an upstanding flange, protruding perpendicularly from the distal surface of the base plate, for attaching the second coupling half in the form of a coupling ring provided on the stomal output collecting bag. In one embodiment, the annular ring is attached to the distal surface of the backing layer. In embodiments, the first coupling half is attached to the distal surface of the backing layer by an adhesive or by welding, but other ways of attaching are acceptable. In embodiments, the first coupling half is attached to a distal surface of the base plate at a location radially farther away from the stoma-receiving opening than any location of one or more detection sensors of the sensor element.

In embodiments, the first half of the coupling means is provided on a separate connection component. In embodiments, the separate component is adapted to further include a housing for the control unit interface. In embodiments, the separate connection component is an injection-moulded component. In embodiments, the connection component further includes a plurality of openings adapted for attachment of an ostomy belt. In embodiments, the housing for the control unit interface is adapted to include means for repeated connections and disconnections of the control unit from the control unit interface. In embodiments, the housing for the control unit interface is further adapted to receive one or more electrode ends of the electrodes of the first and/or second sensor elements. In embodiments, the housing for the control unit provides an electrode terminal for all the electrodes of the first and/or second sensor elements.

In embodiments, the base plate further comprises a first half of a coupling means configured for releasable coupling with a second half of a coupling means on a stomal waste collecting bag. The first half of the coupling means is attached to the distal surface of the backing layer, such that a radial extent of sacrificial material provided on the distal surface of the backing layer is delimited by the first half of the coupling means. The first half of the coupling means can be understood to combine with an edge of the stoma-receiving opening for defining an area of the base plate provided with the sacrificial material. In embodiments, this area or zone provides or is coincident with the center portion of the base plate. Thereby, an outermost rim of the sacrificial material is sealingly engaged with an innermost rim portion of the first half of the coupling means. Thus, in embodiments the radial extent of the sacrificial material does not go, or extend, beyond an innermost portion, such as an internal perimeter of the first half of the coupling means.

In embodiments, a zone or area covered by the sacrificial material coincides with the center portion of the base plate and/or the sensor assembly part. In embodiments, wherein the base plate and/or the sensor assembly part comprises a second sensor element as described herein, the sacrificial material coincides with the center portion of the base plate and/or the sensor assembly part and a single detection sensor of the sensor element locates at a radial distance from the stoma-receiving opening being such that the sensor abuts or is immediately adjacent an innermost portion of the first half of the coupling means, such as at an inner perimeter of an annular coupling ring.

In embodiments, the first sensor element is formed from a stretchable material. Also, each of the electrodes of the first sensor element are configured to be stretchable and adapted to conform to any movements of the stretchable material of the first sensor element. In this disclosure, "stretchable" should be interpreted as a material capable of being easily stretched and resuming former size or shape.

In embodiments, the sacrificial material comprises an adhesive. In other embodiments, the sacrificial material comprises a powder. In other embodiments, the sacrificial material comprises a liquid. In other embodiments, the sacrificial material comprises a gel. In other embodiments, the sacrificial material comprises a plurality of pellets. In yet other embodiments, the sacrificial material comprises a combination of any one or more of an adhesive, a powder, a liquid, a gel and/or a plurality of pellets. These options each provides one or more different advantages including, but not limited to, manipulability, shelf life, suitability for different kinds of stomal output (colostomy output tends to be much more solid than ileo- and urostomy output), processing characteristics and others.

By "neutralizing component" herein is meant a substance capable of neutralizing or at least minimizing the level of skin- or adhesive-aggressiveness of the stomal output. In embodiments, wherein the sacrificial material comprises a neutralizing component, the neutralizing component can comprise a clay, such as organophilic clay, for example bentonite or synthetic clay such as laponite. In embodiments, the neutralizing component may be potato-derived inhibitors or protease inhibitors. Examples of potato-derived inhibitors such as potato protein are disclosed in EP 1 736 136.

In embodiments, the sacrificial material is in the form of a matrix composition with a neutralizing component incorporated. The neutralizing component can be dissolved in the matrix composition or it can be dispersed as particles in the matrix. In embodiments, the matrix can be in the form of coated neutralizing component particles.

In embodiments, the matrix is designed to release neutralizing component to the environment when the matrix is exposed to certain conditions. Such conditions may for example be in the presence of output from the stoma or in the presence of moisture (incl. sweat) as such.

In embodiments, the matrix is in the form of a gel, foam, film layer or paper or a coating.

In embodiments, a suitable example of a matrix composition could be an adhesive comprising 50% w/w polyisobutylene (PIB) and 25% w/w CMC and 25% w/w pectin.

In embodiments, a matrix composition in the form of a water-soluble film can be a PVOH based thermoplastic film, such as a Monosol® 7031 film from kurakay WS Film Division™, Portage, Ind., United States.

In embodiments, the matrix is soluble in water or a component of the stomal output. It may be slowly soluble, by slowly is herein meant that the matrix layer will not be washed away instantly, but will slowly dissolve during wear time of the wafer.

In embodiments, the matrix can absorb moisture and turn into a gel like material when wetted. The gel may be delivered in dry form but swell into a gel when brought into contact with moisture. The gel may be slowly soluble in water or in a component of the output or it may be insoluble, but able to release the neutralizing component when exposed to the output or moisture.

In embodiments, the matrix comprises polysaccharides and/or hydrocolloids. The polysaccharides or hydrocolloids may dissolve or hydrate when exposed to stomal output, thereby releasing the neutralizing component.

In embodiments, the matrix comprises protein. In embodiments, the matrix comprises gelatine.

In embodiments, the matrix is a material capable of forming a gel when wetted. Examples of suitable materials for the matrix composition may be polyethylene glycol (PEG), polyvinyl alcohol (PVA), polyvinyl pyrrolidone (PVP), ethylene vinyl acetate (EVA) based matrix and hydrocolloids such as CMC or gelatine. In embodiments, the matrix is substantially non-adhesive. By non-adhesive is meant that it is not adhesive, though it may under certain circumstances become slightly sticky.

A second aspect of the disclosure concerns a system for determining and signaling moisture propagation in an adhesive material layer of a base plate and/or a sensor assembly part for an ostomy appliance. The system according to the second aspect comprises the base plate and/or the sensor assembly part according to the embodiments of the first aspect of this disclosure, and a control unit configured for connection with the control unit interface of the base plate and/or the sensor assembly part. In embodiments, the control unit is adapted to measure or detect a change. This can include, in one sense, that input received from the first sensor changes to be significantly different from input received from the second sensor. In embodiments, the input received from a sensor resembles or corresponds values for resistance of the material of the base plate and/or the sensor assembly part measured between the conductor electrode and the ground electrode at each of the first sensor and the second sensor. In some implementations, the resistance of the material of the base plate and/or the sensor assembly part between the electrodes before it is engaged by moisture, is of such magnitude that an actual measurement or determination is irrelevant. Instead, under such conditions, the sensor's detection can be seen as an either/or indication—when no moisture has reached the relevant sensor, the resulting reading is "off". Conversely, when the relevant sensor is engaged by moisture, the resulting reading is "on" and provided as a real value.

If/when a significant change in measured resistance occurs, particularly materializing as an abrupt drop in the resistance of material of the base plate and/or the sensor assembly part only at the first (detection) sensor, this signals a sudden increase in the quantity of moisture (incl. in liquid form) present in the adhesive material at the first sensor, but not (yet) in the adhesive material at the second (reference) sensor. The sudden drop in resistance occurs because the suddenly increased quantity of moisture creates a direct and much more preferred conductive path for electrical current to run between the electrodes of the detection sensor, than through the material of the sensor element. If the reference sensor does not measure a similar abrupt change, it means that the increase in moisture level is not also present at the location of the reference sensor. The determination by the control unit of this moisture propagation pattern likely represents a beginning leakage. However, the pattern further indicates that the increase in moisture level (e.g. leakage) has not progressed as far from the stoma-receiving opening as the location of the reference sensor. The user is thereby provided with an "early" warning, allowing him/her enough time to replace the ostomy appliance (or take other measures) and avoid a severe leakage incident.

In embodiments, the measured parameter is the electrical resistance (resistivity) of the material of the sensor element between the conductor electrode and the ground electrode of each sensor. Immediately after application of the adhesive of the base plate and/or the sensor assembly part to the skin surface, the detection sensor and the reference sensor each will detect a certain initial value for the resistance. In embodiments, the electrodes of each of the individual sensors are provided with identical distances between them. Thus, in embodiments, the measured resistance between the electrodes of the first (detection) sensor will be generally identical to the measured resistance between the electrodes of the second (reference) sensor. As described above, this resistance may of such a magnitude that an actual reading of a value when no moisture is present, is irrelevant.

Over time, the skin surface of the user will secrete moisture. Assuming that the moisture secreting of the skin will generally be of the same magnitude at the detection sensor and at the reference sensor, the measured resistance assumedly decreases generally at the same steady rate at the location of the detection sensor and at the location of the reference sensor. This is because the adhesive material takes up moisture at a steady pace over its entire area. However, if suddenly the detection sensor measures an abrupt drop in the resistance between the conductor electrode and the ground electrode of the detection sensor, then that sudden drop is indicative of a change in the conductivity of the material between the electrodes due to a drastic moisture or wetness propagation between the electrodes. This detection in turn is likely to be indicative of the presence of stomal output having entered underneath the base plate and/or the sensor assembly part and having begun eroding away adhesive material. Conversely, if the measured resistance at the detection sensor and at the reference sensor continues to drop at a steady rate, and/or a sudden drop in resistance between the electrodes of the reference sensor is experienced, then this is likely to be indicative of the base plate and/or the sensor assembly part having "wetted steadily up" and reached, or almost reached, an end of life condition requiring replacement.

In embodiments, the control unit can be adapted to measure a change in resistance between two or more detection sensors and/or the reference sensor. Other parameters and/or factors than resistance can be measured to determine changes representing moisture propagation, including, but not limited to, measuring a change in electrical conductivity.

In embodiments, knowing the distance between each of a plurality of individual detection sensors can additionally help provide an indication of the pace of the moisture propagation, which in turn can help determine the nature and severity of the moisture propagation. In addition, the pace of moisture propagation can further be correlated with empirical data to help make the determination. In embodiments, analysis of such empirical data forms part of the basis for providing one or more customized algorithms for application in the control unit, such that the control unit is adaptable to distinguish and determine between a variety of different moisture propagation patterns in the base plate and/or the sensor assembly part. Thus, in embodiments, the control unit is configured to distinguish between different patterns of moisture propagation in the first and/or second layer of adhesive material of the base plate and/or the sensor assembly part.

In embodiments, the control unit is configured to categorize analogous or like changes in a measured or determined parameter value between a detection electrode and a reference electrode as a first moisture propagation pattern in a layer of adhesive material of the base plate and/or the sensor assembly part, and to categorize dissimilar changes in the measured or determined parameter value at the detection electrode and the reference electrode as a second, different moisture propagation pattern in the layer of adhesive material.

In embodiments, the control unit is further adapted to treat the first moisture propagation pattern as a normal moisture propagation pattern, and to treat the second, different moisture propagation pattern as an unusual moisture propagation pattern.

In embodiments, the control unit is configured to give off a signal in response to some, but not all, determined patterns of moisture propagation in the first and/or second layer of adhesive material. Particularly, but not exclusively, in embodiments, the control is configured to give off a signal in response to the detection or determination of an unusual moisture propagation pattern. In embodiments, the control unit is further configured to provide a special indication signal if an unusual moisture propagation pattern is determined. In embodiments, the signal is an alarm signal provided directly by the control unit. In embodiments, the alarm signal can be any one or more of an audible, a visible or a tactile signal. In embodiments, the control unit is configured to give off a data signal and transmit it to another entity, such as a data receiving unit and/or data storage and/or a data processing system. In embodiments, the system according to the second aspect further includes a data processing system adapted to receive, collect and store data and provide for the performance of analyses of the data, and generate an output which forms part of a basis for further optimizing one or more moisture propagation pattern algorithms on an individual user basis, which optimized algorithms can be input into the control unit for future improved precision of the system.

In embodiments, the control unit is configured to provide a normal operation signal when a normal moisture propagation pattern is determined. The control unit can be configured to give off a continuous audible or visible signal at all times during detection of normal patterns. Alternatively, the control unit can be configured to give off a normal operation signal at periodic intervals. In embodiments, the control unit is configured to give off a significantly different audible or visible signal if a change in measured parameter is detected or determined. In embodiments, the control unit can be configured to give off a differentiated warning signal depending on and relative to the severity of the detected moisture propagation pattern (i.a. if a very rapid response by the user is required, the warning signal can be configured to be much more insisting than if more time is available to the user).

In embodiments, the control unit further comprises an integrated power unit. In embodiments, the integrated power unit provides for the control unit to be independent of outside power sources. Moreover, in embodiments, the integrated power unit helps provide for the control unit to be adapted as a re-useable component or entity that is separable from the base plate and/or the sensor assembly part, such that when a base plate and/or a sensor assembly part is replaced, the control unit is simply removed or disconnected from the control unit interface of the "old" base plate and/or the sensor assembly part/appliance and subsequently connected to the control unit interface of the "new" base plate and/or the sensor assembly part having been attached to the user's skin surface. In embodiments, the system further comprises a separate base unit configured to receive and communicate with the control unit, at least during appliance replacements. In embodiments, the system comprises two or more interchangeable control units providing for at least one control unit being available for connection to the base plate and/or the sensor assembly part at all times.

In embodiments, the integrated power unit comprises a battery or a piezoelectric element. In embodiments, the battery is configured as a rechargeable battery. In embodiments, the rechargeable battery is adapted to be recharged when the control unit is connected to the separate base unit, i.a. during appliance replacement.

In embodiments, the system comprises means for connecting the control unit to the control unit interface of the base plate, which means is/are adapted for repeated connections and disconnections of the control unit from the control unit interface of the base plate. In one embodiment, the means comprise first and second magnetic coupling halves for easy and intuitive coupling of the control unit to the base plate. Other reliable and intuitive coupling types are acceptable.

In embodiments, the control unit further comprises means for wireless data communication with a data receiving unit. In embodiments, the means for wireless data communication comprises a Near Field Communication (NFC) unit. Alternatively, a wired connection for the communication and/or transfer of data can be used.

In embodiments, the system further comprises a separate data receiving unit configured for wireless or wired data communication with the control unit.

In embodiments, the control unit and/or the means for wireless data communication is/are configured to communicate relevant processed data to a customized software application provided on a portable electronic device. In embodiments, the control unit is configured to send data and/or a warning signal to an application software ("App") on the user's portable electronic device, such as a watch, smart phone or tablet. In embodiments, the units and components of the system of the second aspect are adapted to communicate via a Bluetooth® connection.

It is further to be understood, that the sensitivity of the system to moisture including outflowing stomal output fluids and slowly secreting moisture, such as sweat, from the skin surface, as well as the system's preferred functionalities, can be adapted to include solutions according to one or more or all of the embodiments disclosed herein. Thereby, particular embodiments of the first and second aspects, can be mixed and/or combined to meet different user requirements. One non-limiting example is to provide a base plate comprising both a first sensor element particularly directed to detect rapid emerging moisture propagation ("direct leakage"/outflow of stomal fluid), and a second sensor element particularly directed to detect the degree of erosion of a sacrificial material applied to further protect the load carrying adhesive layer of the base plate. Moreover, these features can further be combined with one or more customized algorithms provided in the control unit. Thereby, increased precision in detecting or determining a rest-of-life or time-until-replacement of the base plate can be achieved. This is turn helps the user to avoid severe and embarrassing leakage incidents.

In a further aspect, the disclosure relates to the use of the system according to the second aspect for determining and signaling moisture propagation in a material layer of a base plate for an ostomy appliance according to the first aspect. In a further use embodiment, the material layer is an adhesive material. In a further use embodiment, the material is a material optimized to function as a sacrificial material to slow down erosion of the layer of adhesive material of the base plate, which carries the weight of the ostomy appliance and adheres it to the user's skin surface.

DETAILED DESCRIPTION OF THE DRAWINGS

FIG. 1 is an exploded, perspective view of one embodiment of a base plate 20 according to the first aspect of the disclosure.

The base plate 20 comprises a backing layer 24 having a distal surface 26 and a proximal surface 28. A first sensor element 34 is provided between the proximal surface 28 of the backing layer 24 and a first layer of adhesive material 22. FIG. 1 further illustrates embodiments wherein a second sensor element 78 is provided between the distal surface 26 of the backing layer 24 and a connection component 31 including a first half 92 of coupling means 94 for attaching a collecting bag to the base plate 20 for collection of body waste material. The connection component 31 further includes a housing 33 forming an electrode terminal configured to combine with the control unit interface 39 of the first sensor element 34. In the illustrated embodiment, it is to be understood that the housing 33 aligns with the extension portion 48 of the first sensor element 34 and with the extension portion 88 of the second sensor element 78. FIG. 1 further illustrates the stoma-receiving opening 30 of the base plate. A plurality of ostomy belt connections 35 are visible on the connector component 31. Moreover, FIG. 1 illustrates a plurality of through-going openings 66 provided in the first layer of adhesive material 22. Also indicated is the proximal surface 62 of the first layer of adhesive material 22. In embodiments, the backing layer 24 is provided with a through-hole 25 for providing a passageway for the electrodes of the first sensor element 34 to engage with the control unit interface 39 at the electrode terminal in housing 33. In FIG. 1, the first and second sensor elements 34, 78 are provided as a layer or sheet component 56, 79.

As previously described, some parts of the illustrated base plate 20, may be provided as a separate assembly to be applied to an existing base plate, e.g. comprising one or more of the components as described, such as to provide a base plate like the base plate 20 as described. For example, a sensor assembly part 700 may be provided, e.g. comprising the first layer of adhesive material 22, the first sensor element 34, the backing layer 24, and the second sensor element 78. It may be envisioned that the sensor assembly part 700 may be applied to a generic base plate such that said base plate and the sensor assembly part 700 in combination achieves the advantages as disclosed herein.

Figure 2:
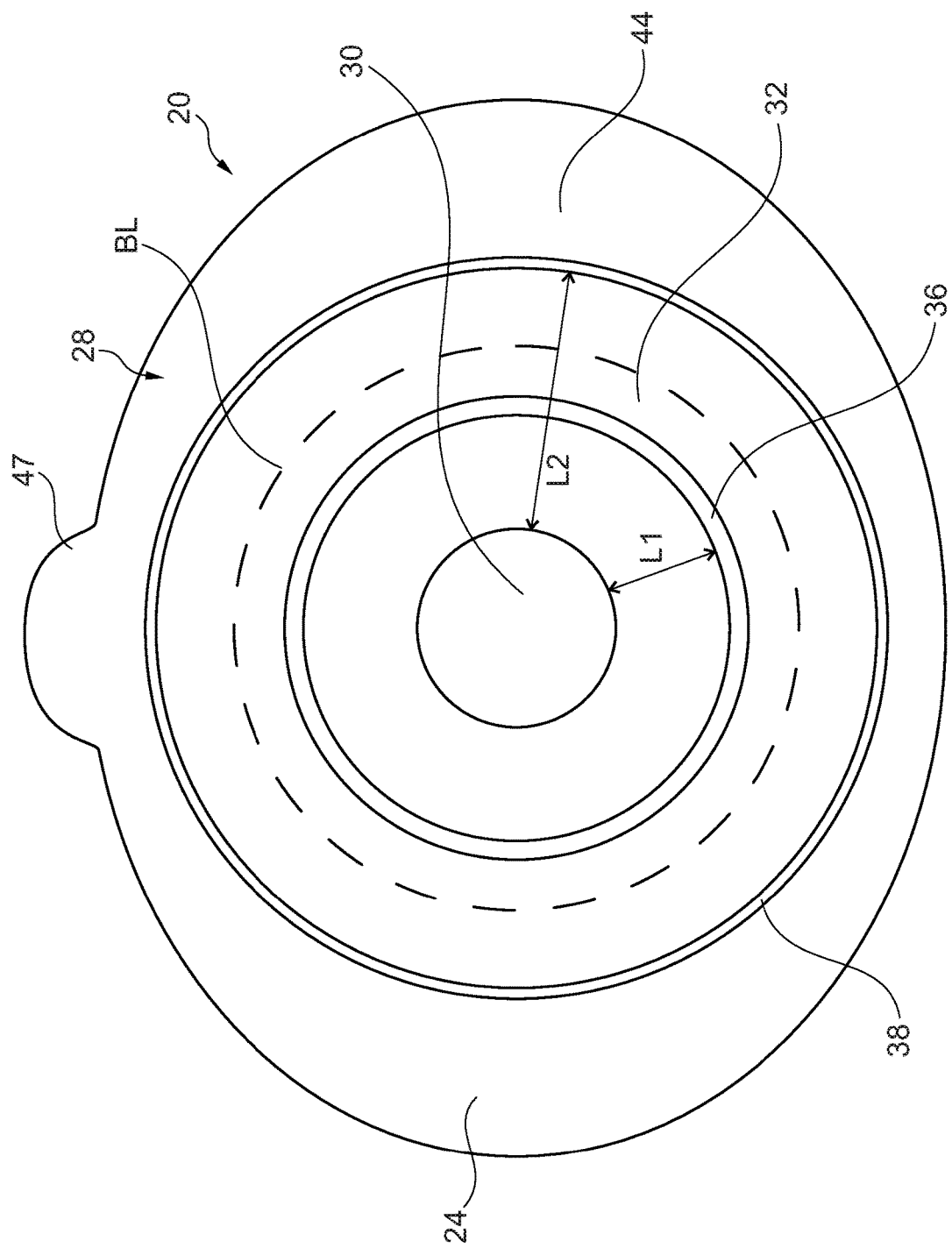
FIG. 2 is a top view of one embodiment of the base plate of the disclosure viewing down on a proximal surface of a backing layer.

FIG. 2 is a top view of one embodiment of the base plate 20 of the disclosure viewing down on the proximal surface 28 of the backing layer 24. In the illustrated embodiment, a first detection sensor 36 and a second reference sensor 38 are provided. For illustration purposes, the first layer 22 of adhesive material (FIG. 1) is not shown. Also, the control unit interface 39 is not indicated. Each of the first detection sensor 36 and the second reference sensor 38 comprises an electrode pair. In the illustrated embodiment, both of the electrode pairs comprise co-extending conductor and ground electrodes. The co-extending electrodes are shown to co-extend with only a short radial distance between them. A broken circular line BL provided annularly around the stoma-receiving opening 30 is shown for illustration purposes: line BL indicates a border between the center portion 32 and an outlying portion 44 of the base plate 20. FIG. 2 illustrates an embodiment wherein a first detection sensor 36 is provided in the center portion 32 of the base plate and the second reference sensor 38 is provided in the outlying portion 44 of the base plate. The second reference sensor 38 is located at a distance L2 from the stoma-receiving opening 30 which is greater than the distance L1 by which the first detection electrode is from the stoma-receiving opening 30. It is to be understood, that in embodiments, a first half 92 of a coupling means 94 can be located on the distal surface 26 (the other side away from the viewer) at approximately a radial distance from the stoma-receiving opening 30 corresponding to where the broken circular line BL is indicated. A pull tab 47 of the backing layer 24 is also shown.

Figure 3:
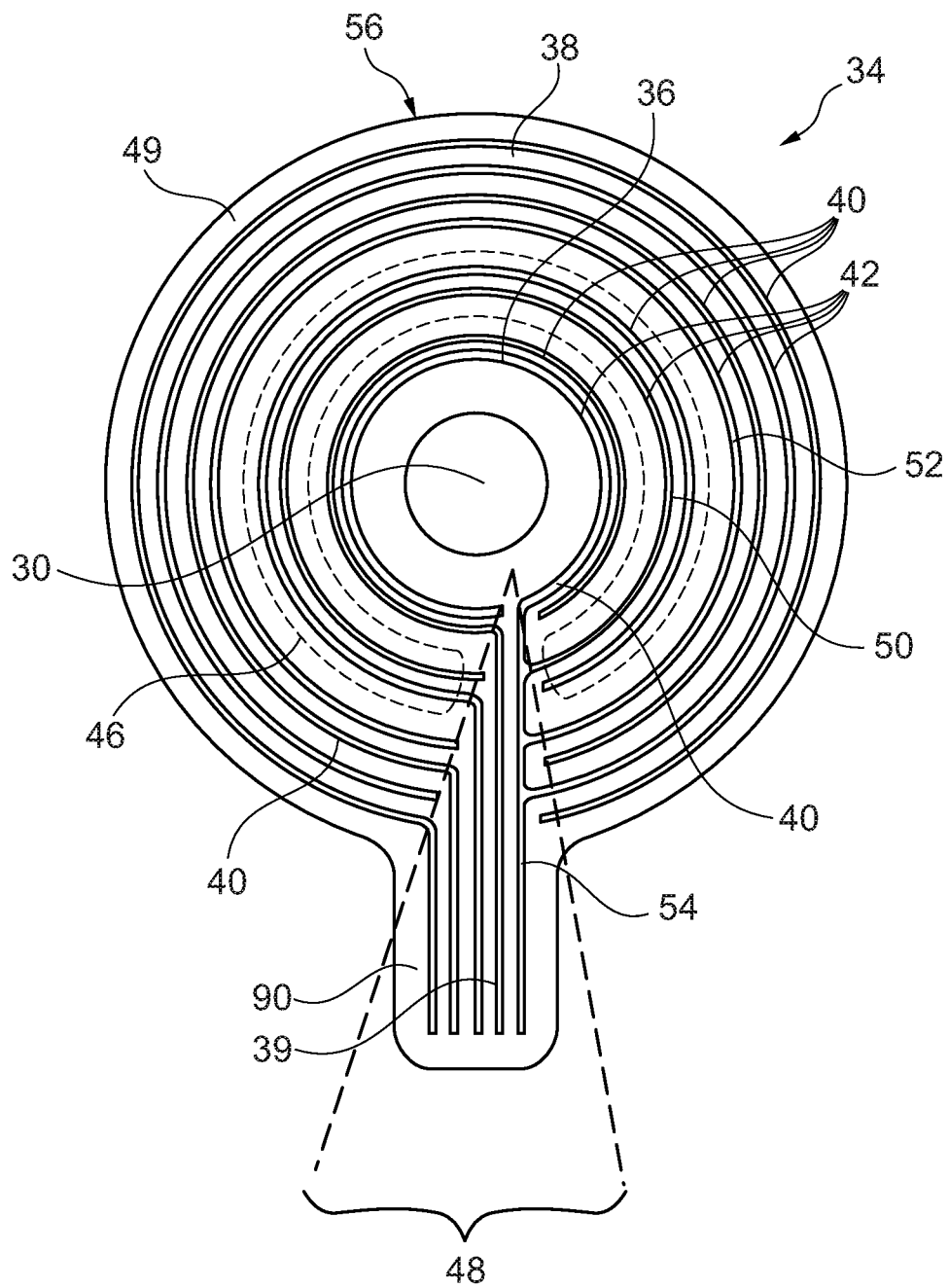
FIG. 3 is a top view of one embodiment of a first sensor element of the base plate.

FIG. 3 is a top view of one embodiment of the first sensor element 34 of the base plate 20 and/or the sensor assembly part. The first sensor element 34 is provided as a layer or sheet component 56. In the illustrated embodiment, the first sensor element 34 includes three detection sensors 36, 50, 52 and reference sensor 38. Each of the sensors 36, 38, 50, 52 includes a conductor electrode 40 and a ground electrode 42. In FIG. 3, all sensors 36, 38, 50, 52 surround the stoma-receiving opening 30 and the sensors are further concentrically arranged in relation to each other. FIG. 3 further schematically indicates and illustrates a detecting portion 46 of each of the sensors 36, 38, 50, 52 (a detecting portion of one sensor is highlighted by a broken line around the sensor) and also illustrates the extension portion 48 of each of the sensors. The extension portion 48 is also highlighted by a triangular shaped broken line resembling a wedge shape. In the illustrated embodiment, each of the conductor electrodes 40 of the sensors extends around the stoma-receiving opening 30 and via the extension portion 48 into a control unit interface 39 of the first sensor element 34. In the embodiment of FIG. 3, each of the ground electrodes 42 extend individually in the detecting portion 46 of the sensors, but combine in a linear, common (shared) ground electrode 54 at the extension portion 48. Also, FIG. 3 shows how the first sensor element 34 comprises a flap portion 90 "cantilevering" off from an outer rim portion 49 of element 34. In FIG. 3, the reference sensor 38 is provided at an outer rim portion 49 of the first sensor element 34.

Figure 4:
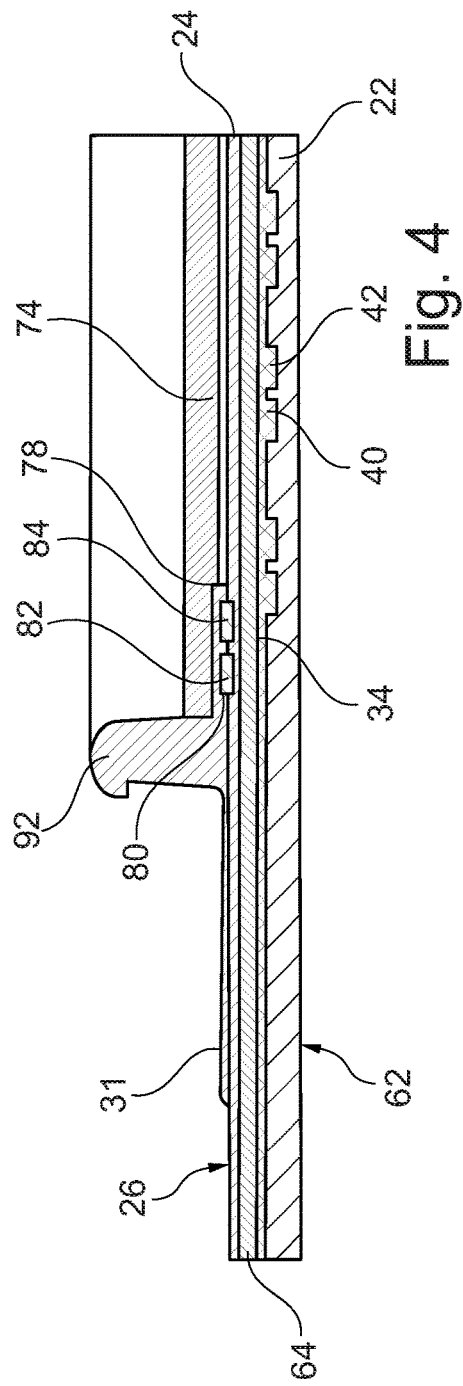
FIG. 4 is a cross-sectional view of a portion of the base plate according to one embodiment.

FIG. 4 is a cross-sectional view of a portion of the base plate according to one embodiment. In the embodiment of FIG. 4, the base plate comprises a first layer of an adhesive material 22 and a second layer of an adhesive material 64. The first sensor element 34 is provided between the first layer of adhesive material 22 and the second layer of adhesive material 64. The electrodes 40, 42 of the detection sensors are provided on a proximal side of the first sensor element 34, such that the electrodes face or contact the first layer of adhesive material 22. FIG. 4 further illustrates a second sensor element 78 provided on the distal surface 26 of the backing layer 24. The electrodes 82, 84 of the single sensor 80 of the second sensor element 78 face or contact the distal surface of the backing layer 24. FIG. 4 further illustrates how a layer of a sacrificial material 74 is provided on the distal surface 26 of the backing layer 24. A portion of the second sensor element 78 including the single sensor 80 is provided between the distal surface 26 of the backing layer 24 and the layer of sacrificial material 74. The extent of the layer of sacrificial material 74 is radially delimited by a first half 92 of a coupling means 94 and by an edge of the stoma-receiving opening (not shown). In the embodiments of FIG. 4, the first half 92 of the coupling means 94 is provided on a connection component 31 attached to the distal surface 26 of the backing layer 24.

Figure 5:
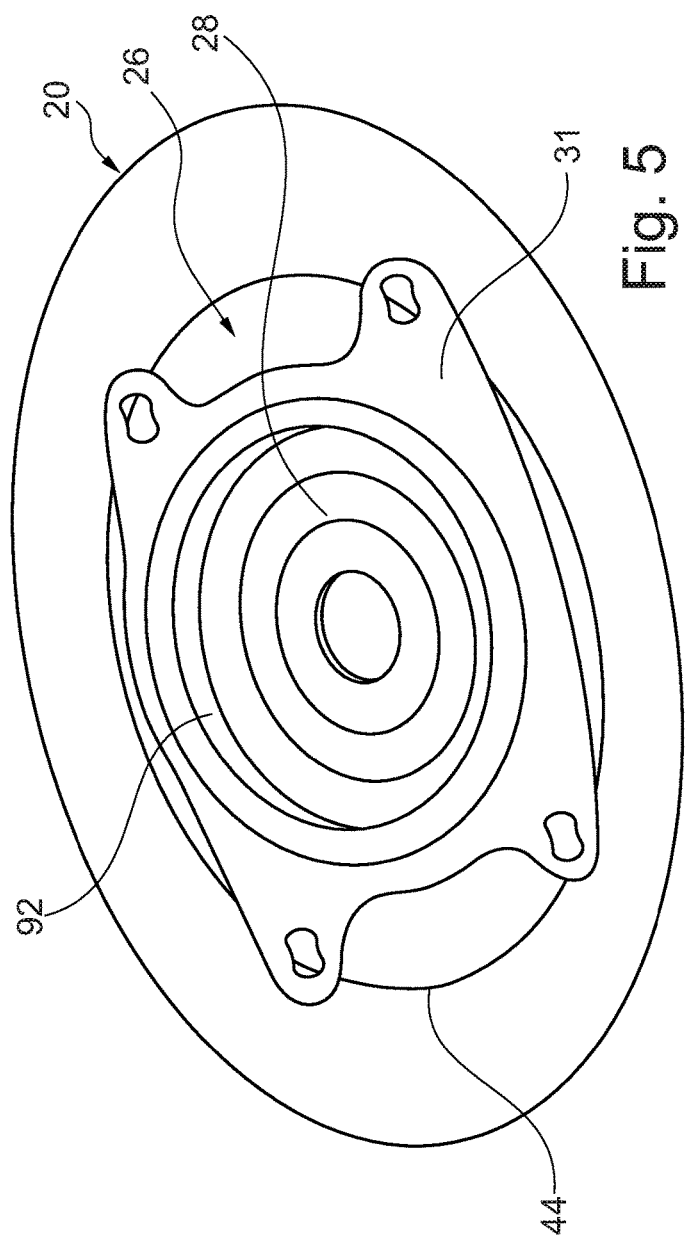
FIG. 5 is a schematic perspective view of a portion of a base plate according to one embodiment.

FIG. 5 is a schematic perspective view of a portion of a base plate 20 according to one embodiment. In FIG. 5, the layer of sacrificial material 74 and the second sensor element 78 are not included. The figure illustrates the center portion 28 of the base plate 20 radially delimited by the first half 92 of the coupling means. Radially beyond the first half 92 of the coupling means, the outlying portion 44 of the base plate is shown. The first half 92 of the coupling means is provided on a connection component 31 which is attached to the distal surface 26 of the backing layer 24.

FIG. 6 is a cross-sectional view of a portion of the base plate according to one embodiment. In FIG. 6, the base plate 20 is basically of similar construction as the embodiment illustrated in FIG. 4. However, the first layer of adhesive material 22 is provided with a plurality of through-going openings 66. The openings 66 provided a passageway 68 through the first layer of adhesive material 22. This embodiment provides for a fast detection of potential adhesive failure and leakage in that the electrodes of a first detection sensor 50 and of a second detection sensor 52 are directly exposed to any moisture incl. aggressive stomal fluids. The number and location of the through-going openings 66 illustrated is only exemplary and can be adapted according to requirements. More than one or all of the sensors can be directly exposed to moisture via passageways 68.

FIG. 7 is a schematic perspective view of one embodiment of the base plate 20 and/or the sensor assembly part 700. FIG. 7 shows the proximal surface 62 of the first layer of adhesive material 22 including a plurality of through-going openings 66. FIG. 7 shows a first group of openings 67 of the plurality of through-going openings 66 radially offset from a second group of openings 69 of the plurality of through-going openings 66. Each through-going opening of the first group 67 provides access to the electrode pair of the first detection sensor 50, and each through-going opening of the second group 69 provides access to one of the electrodes of the first detection sensor 50 and to one of the electrodes of the second detection sensor 52. Thus, the ground electrode of the two detection sensors 50, 52 can be a common shared electrode of first and second detection sensors 50, 52. The number of electrodes and the complexity of the first sensor element 34 is reduced. In FIG. 7, the plurality of through-going openings 66 is distributed circularly around the stoma-receiving opening 30. In the embodiment of FIG. 7, the plurality of openings comprises 24 openings 66.

Figure 8:
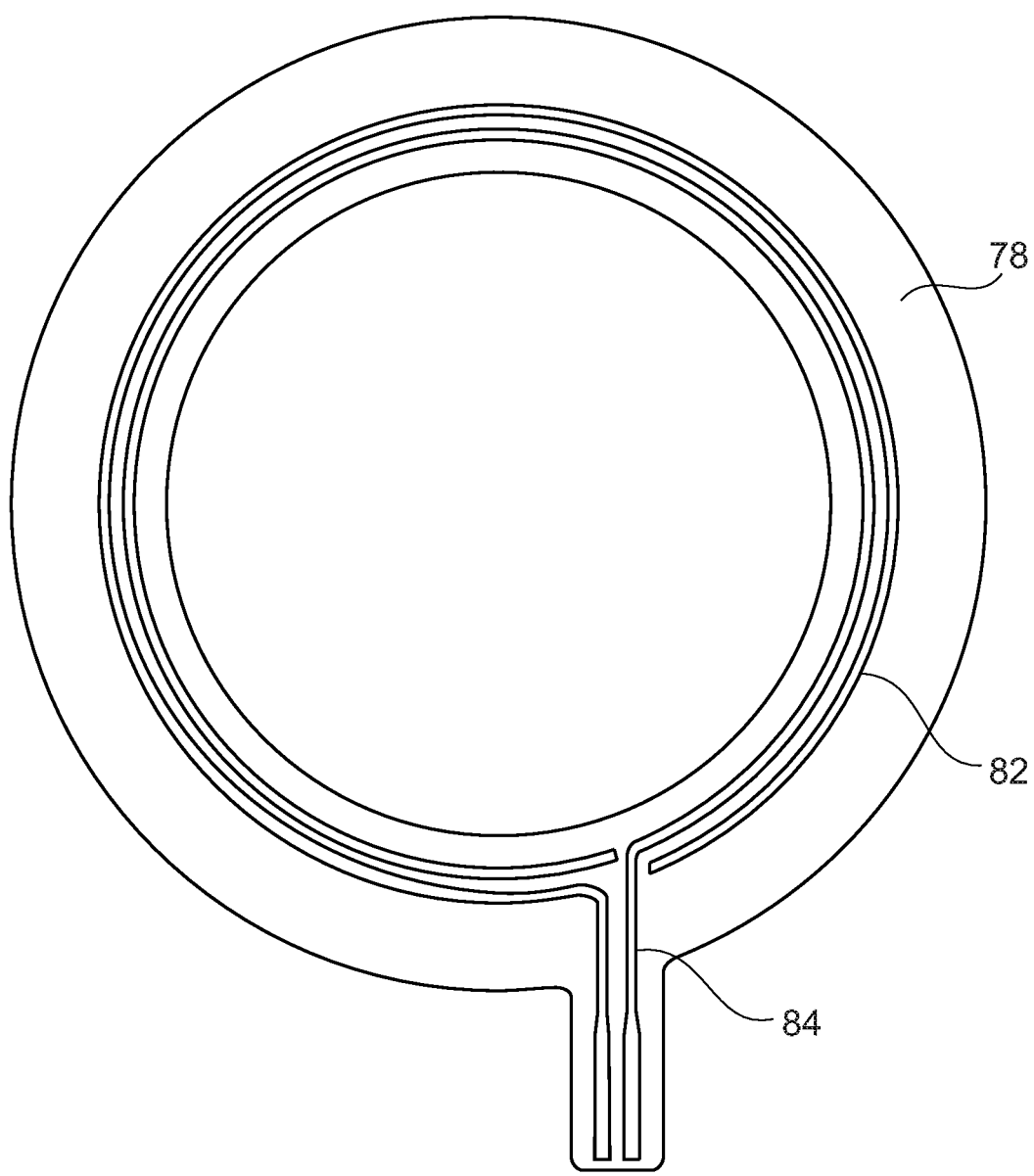
FIG. 8 is a top view of one embodiment of a second sensor element.

FIG. 8 is a top view of one embodiment of a second sensor element 78 having only a single sensor with a pair of co-extending electrodes 82, 84.

Figure 9:
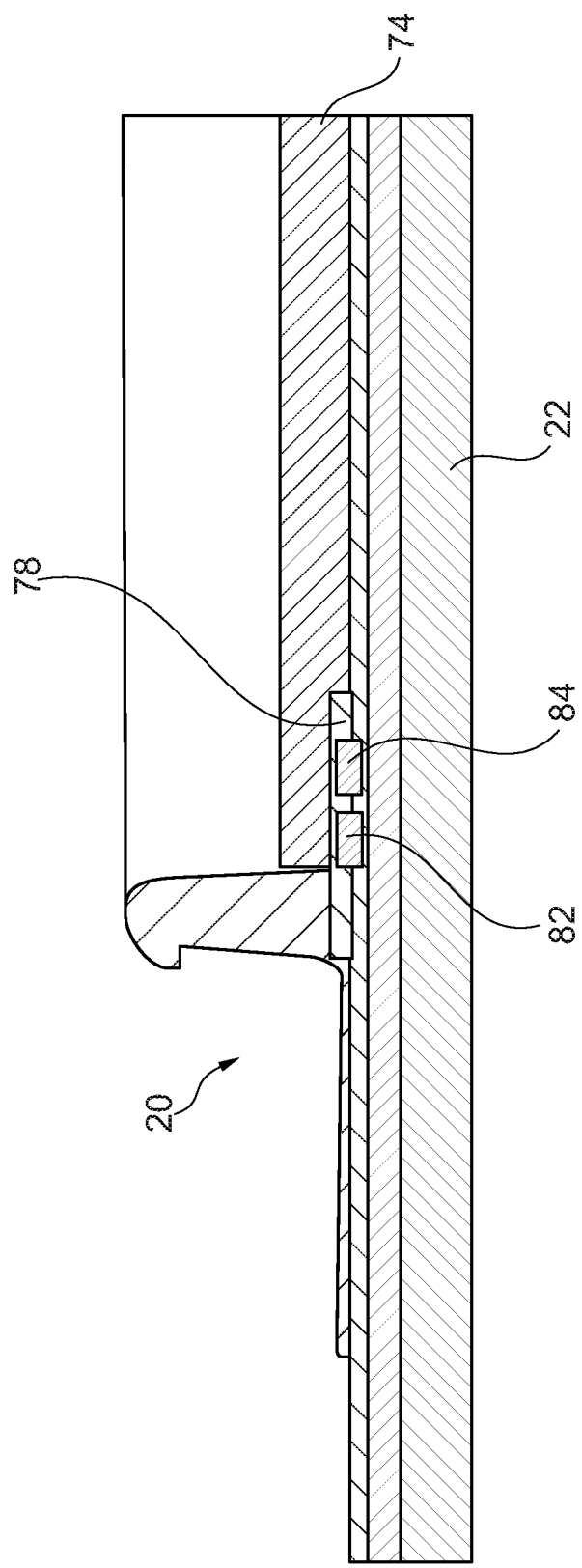
FIG. 9 is a cross-sectional view of a portion of the base plate according to one embodiment.

FIG. 9 is a cross-sectional view of a portion of the base plate 20 according to one embodiment. In the embodiment of FIG. 9, the base plate 20 only includes one sensor with a pair of co-extending electrodes 82, 84 provided in a sensor element 78. The embodiment is directed at being able to detect the level of erosion of the layer of sacrificial material 74 and thus in turn provide an indication of the remaining wear time of the base plate 20 before replacement is needed.

Figure 10:
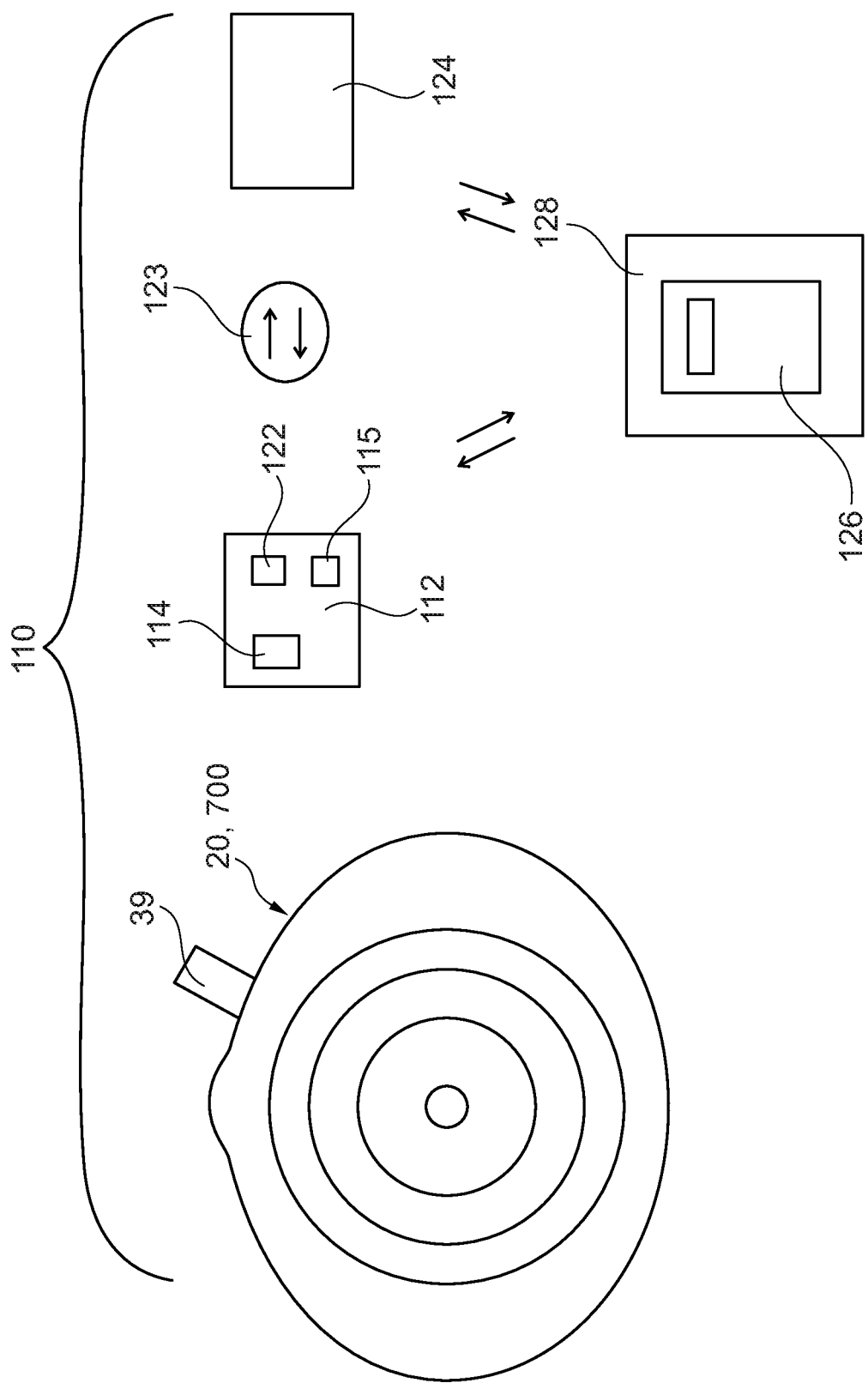
FIG. 10 is a schematic overview of embodiments of a system for detecting moisture propagation in a base plate for an ostomy appliance according to a second aspect of the disclosure.

FIG. 10 is an overview of embodiments of a system 110 for detecting moisture propagation in a base plate 20 and/or a sensor assembly part 700. The system 110 comprises a base plate 20 and/or a sensor assembly part 700 including a control unit interface 39 adapted to be connected to a control unit 112. The control unit 112 includes an integrated power unit 114. The control unit 112 is releasably connected to the control unit interface 39 of the base plate and/or the sensor assembly part, and is configured to be a re-useable component. The control unit 112 further includes instruction processing means 115 which are programmable, e.g. to run one or more algorithms. The control unit 112 includes means 122 for wireless communication 123 with a data receiving unit 124. The data receiving unit 124 can be a separate component as shown, or can be integrated in the control unit 112 or in another separate, external device. The control unit 112 and/or the data receiving unit 114 can communicate with a portable electronic device 128 including a software application 126 for providing input and/or leakage warnings to the user.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

Embodiments

Embodiments of the present disclosure are set out in the following items:

1. A sensor assembly part for an ostomy appliance, comprising:
    optionally a first layer of an adhesive material comprising one or more water soluble or water swellable hydrocolloids adapted for attachment of the sensor assembly part to the skin surface of a user;
    optionally a backing layer comprising a film material forming a distal and a proximal surface of the backing layer;
    wherein the sensor assembly part is configured for being provided with a stoma-receiving opening extending through the sensor assembly part in a center portion of the sensor assembly part; and
    a first sensor element comprising at least one sensor pair, the sensor pair comprising a first sensor and a second sensor, each of the first sensor and the second sensor connected to a control unit interface, such that an electrical signal can be conducted between a respective sensor and the control unit interface;
    wherein the first sensor element is optionally provided between the first layer of adhesive material and the proximal surface of the backing layer;
    wherein each of the first sensor and the second sensor of the sensor pair comprises a conductor electrode and a ground electrode; and
    wherein the second sensor of the sensor pair is located at a greater radial distance from the center portion of the sensor assembly part than the first sensor of the sensor pair.
2. The sensor assembly part of item 1, wherein the conductor electrode and the ground electrode of each of the first sensor and the second sensor form a pair of at least partially co-extending electrodes.
3. The sensor assembly part of item 1 or 2, wherein the at least first sensor is adapted as a detection sensor and configured to detect moisture propagation in the center portion of the sensor assembly part, and the second sensor is adapted as a reference sensor configured to detect moisture propagation in an outlying portion of the sensor assembly part.
4. The sensor assembly part of any one of items 1-3, wherein each of the first and the second sensor comprises:
   a detecting portion provided around the stoma-receiving opening; and
   an extension portion extending from the detecting portion of each sensor to the control unit interface.
5. The sensor assembly part of item 3 or 4, wherein the at least first detection sensor is provided in an at least partly annular configuration around the stoma-receiving opening.
6. The sensor assembly part of item 2, wherein the pair of at least partially co-extending electrodes of each sensor is configured at least partly annularly around the stoma-receiving opening of the sensor assembly part.
7. The sensor assembly part of any one of items 3-6, wherein the at least first detection sensor is located at the center portion of the sensor assembly part.
8. The sensor assembly part of any one of items 3-7, wherein the reference sensor is provided at an outer rim portion of the first sensor element.
9. The sensor assembly part of any one of items 3-8, wherein the reference sensor is provided in an essentially concentric manner around the first detection sensor.
10. The sensor assembly part of any one of items 3-9, wherein the first sensor element comprises one or more additional detection sensors, each of the additional detection sensors being provided at different radial distances from the stoma-receiving opening.
11. The sensor assembly part of any one of items 3-10, wherein the first sensor element comprises two or more detection sensors, the further detection sensor(s) provided concentrically around the first detection sensor and configured such that two detection sensors share one concentrically provided ground electrode.
12. The sensor assembly part of item 11, wherein the at least two detection sensors are provided concentrically in relation to each other.
13. The sensor assembly part of any one of items 4-12, wherein the extension portion comprises a linear, common ground electrode, the linear, common ground electrode connected to a ground electrode of each detection sensor and optionally further connected to the ground electrode of the reference sensor.
14. The sensor assembly part of item 1, wherein the first sensor element comprises a layer or sheet component.
15. The sensor assembly part of item 14, wherein at least a portion of the layer or sheet component is adapted to be moisture permeable.
16. The sensor assembly part of item 14 or 15, wherein the layer or sheet component comprises a planar distal surface and a planar proximal surface, and wherein each sensor is embedded in the layer or sheet component.
17. The sensor assembly part of any one of the preceding items, wherein any proximally facing portion of an electrode is configured to be approximately 1 mm from a proximal surface of the first layer of adhesive material prior to the sensor assembly part being applied to the skin surface.
18. The sensor assembly part of any one of items 14-17, wherein each electrode is provided in one and the same plane of the layer or sheet component.
19. The sensor assembly part of any one of items 1-18, wherein a second layer of adhesive material is provided on the proximal surface of the backing layer, and wherein the first sensor element is provided between the first layer of adhesive material and the second layer of adhesive material.
20. The sensor assembly part of any one of items 3-19, wherein the first layer of adhesive material comprises a plurality of through-going openings, such that each through-going opening provides access to at least one of the electrodes of an electrode pair of a detection sensor by providing a passageway for moisture to pass through the first layer of adhesive material and into contact with the at least one electrode of the detection sensor.
21. The sensor assembly part of any one of items 10-20, wherein a first group of openings of the plurality of through-going openings is radially offset from a second group of openings of the plurality of through-going openings, such that each through-going opening of the first group provides access to the electrode pair of a first detection sensor, and such that each through-going opening of the second group provides access to one of the electrodes of the first detection sensor and to one of the electrodes of a second detection sensor.
22. The sensor assembly part of item 20 or 21, wherein the plurality of through-going openings is distributed in a generally circular configuration around the stoma-receiving opening.
23. The sensor assembly part of any one of items 20-22, wherein the plurality of through-going openings is evenly distributed around the stoma-receiving opening.
24. The sensor assembly part of item 1, further comprising a sacrificial material provided on the distal surface of the backing layer.
25. The sensor assembly part of item 24, wherein the sacrificial material comprises a neutralizing component.
26. The sensor assembly part of item 24 or 25, further comprising a second sensor element provided between the layer of sacrificial material and the distal surface of the backing layer.
27. The sensor assembly part of item 26, wherein the second sensor element comprises one or more sensors each comprising a pair of parallelly extending electrodes defining a detecting portion configured to be located essentially around the stoma-receiving opening, and an extension portion extending from the detecting portion to the control unit interface.
28. The sensor assembly part of item 4, wherein one or more of the backing layer, the first and the second sensor element describes a generally circular figure, and further comprises a flap portion extending radially away from an outermost rim portion of the circular figure.
29. The sensor assembly part of any one of items 4-28, wherein each of the conductor electrodes of each of the pair of electrodes is configured to individually extend through the extension portion from the detecting portion of a respective sensor to the control unit interface, and wherein the ground electrodes of each of the pair of electrodes are configured to combine into a single, common ground electrode, which extends through the extension portion along the individual conductor electrodes from the detecting portion to the control unit interface.

30. A system for determining and signaling moisture propagation in an adhesive material layer of a base plate and/or a sensor assembly part for an ostomy appliance, comprising:
   the sensor assembly part according to any one of items 1-29; and
   a control unit configured for connection with the control unit interface of the sensor assembly part.
31. The system of item 30, wherein the control unit is configured to distinguish between different patterns of moisture propagation in the first and/or second layer of adhesive material of the base plate and/or the sensor assembly part.
32. The system of item 30 or 31, wherein the control unit is configured to give off a signal in response to some, but not all, determined patterns of moisture propagation in the first and/or second layer of adhesive material.
33. The system of any one of items 30-32, wherein the control unit is at least configured to categorize analogous or like changes in a measured or determined parameter value between a detection electrode and a reference electrode as a first moisture propagation pattern in a layer of adhesive material of the base plate and/or the sensor assembly part, and to categorize dissimilar changes in the measured or determined parameter value at the detection electrode and the reference electrode as a second, different moisture propagation pattern in the layer of adhesive material.
34. The system of item 33, wherein the control unit is adapted to treat the first moisture propagation pattern as a normal moisture propagation pattern, and to treat the second, different moisture propagation pattern as an unusual moisture propagation pattern.
35. The system of item 34, wherein the control unit is further configured to provide a special indication signal if an unusual moisture propagation pattern is determined.
36. The system of any one of items 33-35, wherein the control unit is configured to provide a normal operation signal when a normal moisture propagation pattern is determined.
37. The system of any one of items 30-36, wherein the control unit further comprises an integrated power unit.
38. The system of item 37, wherein the integrated power unit comprises a battery or a piezoelectric element.
39. The system of any one of items 30-38, further comprising means for connecting the control unit to the control unit interface of the sensor assembly part which means is/are adapted for repeated connections and disconnections of the control unit from the control unit interface of the sensor assembly part.
40. The system of any one of items 30-39, wherein the control unit further comprises means for wireless data communication with a data receiving unit.
41. The system of item 40, wherein the means for wireless data communication comprises a Near Field Communication unit.
42. The system of item 40 or 41, further comprising a separate data receiving unit configured for wireless data communication with the control unit.
43. The system of any one of items 40-42, wherein the control unit and/or the means for wireless data communication is/are configured to communicate relevant processed data to a customized software application provided on a portable electronic device.
44. Use of the system according to any one of items 30-43 for determining and signaling moisture propagation in a material layer of a sensor assembly part for an ostomy appliance according to any one of items 1-29.
47. Use of the system according to any one of items 32-45 for determining and signaling moisture propagation in an adhesive material layer of a sensor assembly part for an ostomy appliance according to any one of items 1-29.
48. The sensor assembly part of any one of items 1-29, wherein the first sensor element is formed from a stretchable material, and further wherein each of the electrodes of the first sensor element are configured to also be stretchable and adapted to conform to any movements of the stretchable material of the first sensor element.

The invention claimed is:
1. A base plate for a medical appliance, comprising:
   at least a first layer of an adhesive material adapted for attachment of the base plate to the skin surface of a user;
   a backing layer comprising a film material forming a distal and a proximal surface of the backing layer;
   wherein a stoma-receiving opening extending through the base plate is provided in a center portion of the base plate surrounding the stoma-receiving opening; and
   a first sensor element comprising a sheet component comprising at least one sensor pair, the sensor pair comprising a first sensor and a second sensor, each of the first sensor and the second sensor connected to a control unit interface, such that an electrical signal can be conducted between a respective sensor and the control unit interface;
   wherein the first sensor element is provided between the first layer of adhesive material and the proximal surface of the backing layer;
   wherein each of the first sensor and the second sensor of the sensor pair comprises a conductor electrode and a ground electrode printed onto a proximal surface of the sheet component, such that the electrodes of the sensors have direct contact with the adhesive material of the base plate; and
   wherein the second sensor of the sensor pair is located at a greater radial distance from the stoma-receiving opening than the first sensor of the sensor pair.
2. The base plate of claim 1, wherein the conductor electrode and the ground electrode of each of the first sensor and the second sensor form a pair of at least partially co-extending electrodes.
3. The base plate of claim 1, wherein the at least first sensor is adapted as a detection sensor and configured to detect moisture propagation in the center portion of the base plate, and the second sensor is adapted as a reference sensor configured to detect moisture propagation in an outlying portion of the base plate.
4. The base plate of claim 1, wherein each of the first and the second sensor comprises:
   a detecting portion provided around the stoma-receiving opening; and
   an extension portion extending from the detecting portion of each sensor to the control unit interface.
5. The base plate of claim 3, wherein the at least first detection sensor is provided in an at least partly annular configuration around the stoma-receiving opening.
6. The base plate of claim 2, wherein the pair of at least partially co-extending electrodes of each sensor is configured at least partly annularly around the stoma-receiving opening of the base plate.

7. The base plate of claim 3, wherein the at least first detection sensor is located at the center portion of the base plate.

8. The base plate of claim 3, wherein the reference sensor is provided at an outer rim portion of the first sensor element.

9. The base plate of claim 3, wherein the reference sensor is provided in an essentially concentric manner around the first detection sensor.

10. The base plate of claim 3, wherein the first sensor element comprises one or more additional detection sensors, each of the additional detection sensors being provided at different radial distances from the stoma-receiving opening.

11. The base plate of claim 3, wherein the first sensor element comprises two or more detection sensors, the further detection sensor(s) provided concentrically around the first detection sensor and configured such that two detection sensors share one concentrically provided ground electrode.

12. The base plate of claim 11, wherein the at least two detection sensors are provided concentrically in relation to each other.

13. The base plate of claim 4, wherein the extension portion comprises a linear, common ground electrode, the linear, common ground electrode connected to a ground electrode of each detection sensor and optionally further connected to the ground electrode of the reference sensor.

14. The base plate of claim 1, wherein the first sensor element comprises a layer or sheet component.

15. The base plate of claim 14, wherein at least a portion of the layer or sheet component is adapted to be moisture permeable.

16. The base plate of claim 14, wherein the layer or sheet component comprises a planar distal surface and a planar proximal surface, and wherein each sensor is embedded in the layer or sheet component.

17. The base plate of claim 1, wherein any proximally facing portion of an electrode is configured to be approximately 1 mm from a proximal surface of the first layer of adhesive material prior to the base plate being applied to the skin surface.

18. The base plate of claim 14, wherein each electrode is provided in one and the same plane of the layer or sheet component.

19. The base plate of claim 1, wherein a second layer of adhesive material is provided on the proximal surface of the backing layer, and wherein the first sensor element is provided between the first layer of adhesive material and the second layer of adhesive material.

20. The base plate of claim 3, wherein the first layer of adhesive material comprises a plurality of through-going openings, such that each through-going opening provides access to at least one of the electrodes of an electrode pair of a detection sensor by providing a passageway for moisture to pass through the first layer of adhesive material and into contact with the at least one electrode of the detection sensor.

21. The base plate of claim 10, wherein a first group of openings of the plurality of through-going openings is radially offset from a second group of openings of the plurality of through-going openings, such that each through-going opening of the first group provides access to the electrode pair of a first detection sensor, and such that each through-going opening of the second group provides access to one of the electrodes of the first detection sensor and to one of the electrodes of a second detection sensor.

22. The base plate of claim 20, wherein the plurality of through-going openings is distributed in a generally circular configuration around the stoma-receiving opening.

23. The base plate of claim 20, wherein the plurality of through-going openings is evenly distributed around the stoma-receiving opening.

24. The base plate of claim 1, further comprising a sacrificial material provided on the distal surface of the backing layer.

25. The base plate of claim 24, wherein the sacrificial material comprises a neutralizing component.

26. The base plate of claim 24, further comprising a second sensor element provided between the layer of sacrificial material and the distal surface of the backing layer.

27. The base plate of claim 26, wherein the second sensor element comprises one or more sensors each comprising a pair of parallelly extending electrodes defining a detecting portion configured to be located essentially around the stoma-receiving opening, and an extension portion extending from the detecting portion to the control unit interface.

28. The base plate of claim 4, wherein one or more of the backing layer, the first and the second sensor element describes a generally circular figure, and further comprises a flap portion extending radially away from an outermost rim portion of the circular figure.

29. The base plate of claim 1, further comprising a first half of a coupling means configured for releasable coupling with a second half of the coupling means provided on a stomal waste collecting bag, wherein the first half of the coupling means is attached to the distal surface of the backing layer.

30. The base plate of claim 24, further comprising a first half of a coupling means configured for releasable coupling with the second half of a coupling means provided on a stomal waste collecting bag, wherein the first half of the coupling means is attached to the distal surface of the backing layer, such that a radial extent of the sacrificial material is delimited by the first half of the coupling means, whereby an outermost rim of the layer of sacrificial material is sealingly engaged with an innermost rim portion of the first half of the coupling means.

31. The base plate of claim 4, wherein each of the conductor electrodes of each of the pair of electrodes is configured to individually extend through the extension portion from the detecting portion of a respective sensor to the control unit interface, and wherein the ground electrodes of each of the pair of electrodes are configured to combine into a single, common ground electrode, which extends through the extension portion along the individual conductor electrodes from the detecting portion to the control unit interface.

32. A system for determining and signaling moisture propagation in an adhesive material layer of a base plate for a medical appliance, comprising:

the base plate, comprising:
  at least a first layer of an adhesive material adapted for attachment of the base plate to the skin surface of a user;
  a backing layer comprising a film material forming a distal and a proximal surface of the backing layer;
  wherein a stoma-receiving opening extending through the base plate is provided in a center portion of the base plate surrounding the stoma-receiving opening; and
  a first sensor element comprising a sheet component comprising at least one sensor pair, the sensor pair comprising a first sensor and a second sensor, each of the first sensor and the second sensor connected to a control unit interface, such that an electrical signal can be conducted between a respective sensor and the control unit interface;

wherein the first sensor element is provided between the first layer of adhesive material and the proximal surface of the backing layer;

wherein each of the first sensor and the second sensor of the sensor pair comprises a conductor electrode and a ground electrode printed onto a proximal surface of the sheet component, such that the electrodes of the sensors have direct contact with the adhesive material of the base plate; and wherein the second sensor of the sensor pair is located at a greater radial distance from the stoma-receiving opening than the first sensor of the sensor pair; and a control unit configured for connection with the control unit interface of the base plate.

33. The system of claim 32, wherein the control unit is configured to distinguish between different patterns of moisture propagation in the first and/or second layer of adhesive material of the base plate.

34. The system of claim 32, wherein the control unit is configured to give off a signal in response to some, but not all, determined patterns of moisture propagation in the first and/or second layer of adhesive material.

35. The system of claim 32, wherein the control unit is at least configured to categorize analogous or like changes in a measured or determined parameter value between a detection electrode and a reference electrode as a first moisture propagation pattern in a layer of adhesive material of the base plate, and to categorize dissimilar changes in the measured or determined parameter value at the detection electrode and the reference electrode as a second, different moisture propagation pattern in the layer of adhesive material.

36. The system of claim 35, wherein the control unit is adapted to treat the first moisture propagation pattern as a normal moisture propagation pattern, and to treat the second, different moisture propagation pattern as an unusual moisture propagation pattern.

37. The system of claim 36, wherein the control unit is further configured to provide a special indication signal if an unusual moisture propagation pattern is determined.

38. The system of claim 35, wherein the control unit is configured to provide a normal operation signal when a normal moisture propagation pattern is determined.

39. The system of claim 32, wherein the control unit further comprises an integrated power unit.

40. The system of claim 39, wherein the integrated power unit comprises a battery or a piezoelectric element.

41. The system of claim 32, further comprising means for connecting the control unit to the control unit interface of the base plate which means is/are adapted for repeated connections and disconnections of the control unit from the control unit interface of the base plate.

42. The system of claim 32, wherein the control unit further comprises means for wireless data communication with a data receiving unit.

43. The system of claim 42, wherein the means for wireless data communication comprises a Near Field Communication unit.

44. The system of claim 42, further comprising a separate data receiving unit configured for wireless data communication with the control unit.

45. The system of claim 42, wherein the control unit and/or the means for wireless data communication is/are configured to communicate relevant processed data to a customized software application provided on a portable electronic device.

46. Use of the system according to claim 32 for determining and signaling moisture propagation in a material layer of a base plate for an medical appliance according to claim 1.

47. Use of the system according to claim 32 for determining and signaling moisture propagation in an adhesive material layer of a base plate for an medical appliance according to claim 1.

48. The base plate of claim 1, wherein the first sensor element is formed from a stretchable material, and further wherein each of the electrodes of the first sensor element are configured to also be stretchable and adapted to conform to any movements of the stretchable material of the first sensor element.

* * * * *